US011503859B2

(12) United States Patent
Hu

(10) Patent No.: US 11,503,859 B2
(45) Date of Patent: Nov. 22, 2022

(54) ELECTRONIC ATOMIZING DEVICE AND ATOMIZER AND A LIQUID INJECTION STRUCTURE THEREOF

(71) Applicant: Jiangmen Moore Technology.,Ltd, Jiangmen (CN)

(72) Inventor: Weiguang Hu, Jiangmen (CN)

(73) Assignee: Jiangmen Moore Technology., Ltd, Jiangmen (CN)

( * ) Notice: Subject to any disclaimer, the term of this patent is extended or adjusted under 35 U.S.C. 154(b) by 363 days.

(21) Appl. No.: 16/987,327

(22) Filed: Aug. 6, 2020

(65) Prior Publication Data
US 2021/0045442 A1 Feb. 18, 2021

(30) Foreign Application Priority Data
Aug. 13, 2019 (CN) .......................... 201910745080.6

(51) Int. Cl.
*A24F 13/00* (2006.01)
*A24F 17/00* (2006.01)
(Continued)

(52) U.S. Cl.
CPC .............. *A24F 40/42* (2020.01); *A24F 40/10* (2020.01); *B05B 17/00* (2013.01); *A61M 15/06* (2013.01)

(58) Field of Classification Search
CPC ........ A24F 40/10; A24F 40/42; A24F 40/485; A61M 11/042; A61M 15/0023;
(Continued)

(56) References Cited

U.S. PATENT DOCUMENTS 5,249,611 A 10/1993 Law
10,412,785 B1 * 9/2019 Schwartz ................. H05B 3/06
(Continued)

FOREIGN PATENT DOCUMENTS

CN 205125041 U 4/2016
CN 206079036 U 4/2017
(Continued)

OTHER PUBLICATIONS

The extended European search report of EP application No. 18208704.9 dated Jul. 2, 2019.
(Continued)

*Primary Examiner* — Abdullah A Riyami
*Assistant Examiner* — Thang H Nguyen
(74) *Attorney, Agent, or Firm* — Andrew C. Cheng

(57) ABSTRACT

The disclosure relates to an electronic atomizing device and an atomizer and a liquid injection structure thereof. The liquid injection structure includes an outer pipe provided with an exhaust port and a liquid injection assembly including a sleeve pipe disposed in the outer pipe and a liquid injection pipe disposed in the sleeve pipe. The liquid injection pipe is provided with a liquid injection port, and is axially movable relative to the sleeve pipe between a first position where the sleeve pipe seals the liquid injection port and a second position where the seal of the liquid injection port by the sleeve pipe is released. The sleeve pipe is axially movable relative to the outer pipe between a third position where the sleeve pipe seals the exhaust port and a fourth position where the seal of the exhaust port by the sleeve pipe is released.

20 Claims, 11 Drawing Sheets

(51) Int. Cl.
  *A24F 25/00* (2006.01)
  *A24F 40/42* (2020.01)
  *B05B 17/00* (2006.01)
  *A24F 40/10* (2020.01)
  *A61M 15/06* (2006.01)

(58) Field of Classification Search
  CPC .......... A61M 15/06; A61M 2202/0468; A61M 2205/8206; A61M 2209/045; B05B 11/0056; B05B 17/00
  See application file for complete search history.

(56) References Cited

U.S. PATENT DOCUMENTS

| | | | |
|---|---|---|---|
| 11,006,672 B2* | 5/2021 | Wei | A24F 40/485 |
| 2016/0198771 A1* | 7/2016 | Goggin | H05B 3/44 |
| | | | 131/329 |
| 2017/0065001 A1* | 3/2017 | Li | F16K 15/14 |
| 2017/0156408 A1* | 6/2017 | Li | A24F 40/40 |
| 2017/0196272 A1* | 7/2017 | Li | A24F 40/40 |
| 2017/0208869 A1* | 7/2017 | Li | A24F 40/485 |
| 2018/0035718 A1* | 2/2018 | Liu | A24F 40/485 |
| 2018/0279683 A1* | 10/2018 | Qiu | A24F 40/42 |
| 2018/0360126 A1* | 12/2018 | Chen | A24F 40/42 |
| 2020/0375655 A1* | 12/2020 | Axelsson | A61B 18/1445 |
| 2021/0251298 A1* | 8/2021 | Qiu | A24F 40/57 |
| 2021/0259310 A1* | 8/2021 | Qiu | B67D 7/0288 |
| 2021/0298356 A1* | 9/2021 | Qiu | B65B 39/00 |
| 2022/0248754 A1* | 8/2022 | Liu | A24F 40/40 |

FOREIGN PATENT DOCUMENTS

| | | |
|---|---|---|
| CN | 105231492 B | 9/2018 |
| CN | 105192896 B | 10/2018 |
| CN | 208338874 U | 1/2019 |
| WO | 2018046530 A1 | 3/2018 |

OTHER PUBLICATIONS

Notice of allowance of U.S. Appl. No. 16/158,322 dated Feb. 10, 2021.

* cited by examiner

ELECTRONIC ATOMIZING DEVICE AND ATOMIZER AND A LIQUID INJECTION STRUCTURE THEREOF

TECHNICAL FIELD

The present disclosure relates to the field of atomization, and more particularly, to an electronic atomizing device and an atomizer and a liquid injection structure thereof.

BACKGROUND

Electronic cigarettes are also known as virtual cigarettes or electronic atomizing devices. As substitutes for conventional cigarettes, the electronic cigarettes are often used for quitting smoking. With similar appearance and flavor to conventional cigarettes, the electronic cigarettes are generally free of harmful chemicals like tar or aerosol in the cigarettes.

The electronic atomizing device mainly includes an atomizer and a power supply device. The existing atomizers are mainly divided into disposable atomizers and refillable atomizers. The refillable atomizers can be refilled with liquid to realize continuable use after the liquid is used up. A conventional refillable atomizer mainly includes a liquid storage cavity and a liquid injection structure disposed on a wall of the liquid storage cavity to inject liquid into the liquid storage cavity. An existing liquid injection structure mainly includes an outer pipe and a liquid injection pipe disposed in the outer pipe, and a liquid injection port is opened by pressing the liquid injection pipe for liquid injection. However, since the liquid injection port is usually disposed at the bottom of the outer pipe, the depth of the liquid injection port is quite deep, resulting in a relatively large amount of liquid remaining in the pipe after the injection is finished, which is difficult to clean. In addition, since there is no seal between an outer end of the outer pipe and the liquid injection pipe, it is easy to cause leakage of the liquid, thereby causing trouble to consumers.

SUMMARY

In order to solve the above technical problems, the present disclosure provides an improved electronic atomizing device and an atomizer and a liquid injection structure thereof.

In order to solve these technical problems, the present disclosure provides the following technical solutions: a liquid injection structure for an atomizer, wherein the liquid injection structure includes an outer pipe and a liquid injection assembly disposed in the outer pipe; the outer pipe is provided with an exhaust port;

the liquid injection assembly includes a sleeve pipe and a liquid injection pipe, and the liquid injection pipe is provided thereon with a liquid injection port;

the liquid injection pipe is axially disposed in the sleeve pipe, and is axially movable back and forth relative to the sleeve pipe between a first position adjacent to an outer end of the outer pipe and a second position away from the outer end of the outer pipe; when the liquid injection pipe is in the first position, the sleeve pipe seals the liquid injection port; when the liquid injection pipe is in the second position, the seal of the liquid injection port by the sleeve pipe is released;

the sleeve is axially disposed in the outer pipe, and is axially movable back and forth relative to the outer pipe between a third position adjacent to the outer end of the outer pipe and a fourth position away from the outer end of the outer pipe; when the sleeve is in the third position, the sleeve seals the exhaust port, and when the sleeve is in the fourth position, the seal of the exhaust port by the sleeve is released.

In some embodiments, the outer pipe includes a first pipe body and a base body disposed at an inner end of the first pipe body; the exhaust port is defined on a side wall of the first pipe body; an outer end of the first pipe body is provided with an opening; an exhaust cavity is defined between an inner wall of the first pipe body and an outer wall of the liquid injection assembly; the exhaust port, the exhaust cavity and the opening are fluidly connected in sequence to form an exhaust passage;

the base body is provided with a liquid inlet; a liquid inlet cavity is defined between an outer wall of the liquid injection pipe and inner walls of the sleeve pipe and the base body; the liquid injection port, the liquid inlet cavity and the liquid inlet are fluidly connected in sequence to form a liquid inlet passage.

In some embodiments, the liquid injection assembly further includes an elastic member; two ends of the elastic member respectively abut against the liquid injection pipe and the base body to elastically maintain the liquid injection pipe in the first position and elastically maintain the sleeve pipe in the third position.

In some embodiments, when the liquid injection pipe is pressed, the liquid injection pipe moves from the first position to the second position to abut against the sleeve pipe, and the liquid injection port fluidly communicates with the liquid inlet, thereby opening the liquid inlet passage; continuing to press the liquid injection pipe, the liquid injection pipe drives the sleeve pipe to move together and enables the sleeve pipe to move from the third position to the fourth position to abut against the base body, and the exhaust port fluidly communicates with the opening, thereby opening the exhaust passage;

when a pressing force on the liquid injection pipe is removed, the liquid injection pipe returns from the second position to the first position under the action of the elastic member, so that the liquid injection port is isolated from the liquid inlet, thereby closing the liquid inlet passage; then, the liquid injection pipe drives the sleeve pipe to return from the fourth position to the third position, so that the exhaust port is isolated from the opening, thereby closing the exhaust passage.

In some embodiments, a friction force between the liquid injection pipe and the sleeve pipe is less than a friction force between the sleeve pipe and the outer pipe.

In some embodiments, the liquid injection structure further includes a first sealing member and a third sealing member;

the first sealing member is disposed on a side wall of the sleeve pipe to isolate the exhaust port from the exhaust cavity, and the third sealing member is disposed on a side wall of the liquid injection pipe to isolate the liquid injection port from the liquid inlet.

In some embodiments, the liquid injection structure further includes a second sealing member, and the second sealing member is fitted at the opening to seal the opening and isolate the exhaust cavity from the opening.

In some embodiments, the liquid injection structure further includes a fourth sealing member provided on a side wall of the liquid injection pipe; the third sealing member and the fourth sealing member are respectively located on two opposite sides of the liquid injection port.

In some embodiments, an inner periphery of the outer end of the first pipe body is radially provided with a second annular retaining ring, and an inner hole of the second annular retaining ring defines the opening;

the second sealing member is disposed on a side of the second annular retaining ring towards the base body, and the second sealing member is in a sealing fit with the second annular retaining ring.

In some embodiments, an inner periphery of an outer end of the sleeve pipe is radially provided with a third annular retaining ring; when the liquid injection pipe is in the first position, an outer end surface of the liquid injection pipe abuts against the third annular retaining ring; and when the liquid injection pipe is in the second position, the outer end surface of the liquid injection pipe is spaced from the third annular retaining ring.

In some embodiments, the sleeve pipe includes a third pipe body axially disposed in the first pipe body and a second pipe body axially inserted at an outer end of the third pipe body; an inner periphery of an outer end of the second pipe body radially extends inwards to form the third annular retaining ring;

the second pipe is externally provided with a first annular retaining ring; an inner end surface of the first annular retaining ring abuts against the third pipe body, and an outer end surface of the first annular retaining ring abuts against the second sealing member;

the first sealing member is sleeved outside the third pipe body, and the third sealing member is in a sealing fit with an inner end surface of the second pipe body.

In some embodiments, the third pipe body includes a first pipe section and a second pipe section disposed at an inner end of the first pipe section; an outer diameter and an inner diameter of the first pipe section are respectively larger than those of the second pipe section, and a second positioning flange is formed at a junction between the first pipe section and the second pipe section;

a fourth positioning flange is provided outside the liquid injection pipe, and an outer end surface of the fourth positioning flange abuts against the third sealing member;

when the liquid injection pipe is in the first position, the third sealing member abuts against an inner end surface of the second pipe body, and the fourth positioning flange is spaced from the second positioning flange; when the liquid injection pipe is in the second position, the third sealing member is separated from the inner end surface of the second pipe body, and the fourth positioning flange abuts against the second positioning flange.

In some embodiments, two ends of the liquid injection pipe extend out of the sleeve pipe respectively, and the second sealing member is disposed on a side wall of the liquid injection pipe.

In some embodiments, the sleeve pipe includes a third pipe section and a fourth pipe section provided at an inner end of the third pipe section; an inner diameter of the third pipe section is less than an inner diameter of the fourth pipe section; a fourth annular retaining ring is formed at a junction between an inner hole of the third pipe section and an inner hole of the fourth pipe section; the third sealing member is in a sealing fit with the fourth annular retaining ring.

In some embodiments, the liquid injection pipe includes a fourth pipe body and a fifth pipe body sleeved outside an inner end of the fourth pipe body; the liquid injection port is defined on the fourth pipe body; the second sealing member is sleeved outside the fourth pipe body, and the third sealing member is sleeved outside the fifth pipe body.

In some embodiments, a sixth positioning flange is provided outside the fourth pipe body; an outer end surface of the sixth positioning flange abuts against the second sealing member, and an inner end surface of the sixth positioning flange movably abuts against an outer end surface of the sleeve pipe;

an eighth positioning flange is provided outside the fifth pipe body; an outer end surface of the eighth positioning flange abuts against the third sealing member, and an inner end surface of the eighth positioning flange abuts against the elastic member.

In some embodiments, the liquid injection pipe includes a main body and a positioning member detachably sleeved outside the main body; an outer end surface of the positioning member abuts against the third sealing member, and an inner end surface of the positioning member abuts against the elastic member.

The present disclosure further provides an atomizer, including a liquid storage cavity and the liquid injection structure according to any one of the above, wherein the liquid injection structure is disposed on a cavity wall forming the liquid storage cavity; a liquid inlet and an exhaust port of the liquid injection structure are respectively in fluid communication with the liquid storage cavity.

In some embodiments, the atomizer further includes an atomization unit and a suction nozzle slidably disposed at one end of the atomization unit; the atomization unit is provided therein with the liquid storage cavity; the suction nozzle is able to move back and forth relative to the atomization unit between a fifth position and a sixth position;

the liquid injection structure is disposed at an end of the atomization unit towards the suction nozzle; when the suction nozzle is in the fifth position, the liquid injection structure is shielded by the suction nozzle; and when the suction nozzle is in the sixth position, the liquid injection structure is exposed.

The present disclosure further provides an electronic atomizing device, including a power supply device and the atomizer according to any one of the above, wherein the atomizer is electrically connected to the power supply device.

The electronic atomizing device and the atomizer and the liquid injection structure thereof in the present disclosure have at least the following beneficial effects: With the special configuration of the liquid injection structure, the liquid injection port on the liquid injection pipe is much closer to an outer surface of the product, that is, the position of the liquid injection port on the liquid injection pipe is much closer to the outer end surface of the liquid injection structure. Therefore, the liquid medium remaining in the pipe after injection can be reduced as much as possible, and the cleaning is much easier.

In addition, in a non-injection state, a seal is maintained between the outer end of the outer pipe and the liquid injection assembly to avoid leakage of the liquid medium, thereby improving the user experience.

BRIEF DESCRIPTION OF DRAWINGS

The present disclosure is described in further detail below with reference to the accompanying drawings and embodiments.

DETAILED DESCRIPTION

Figure 1:
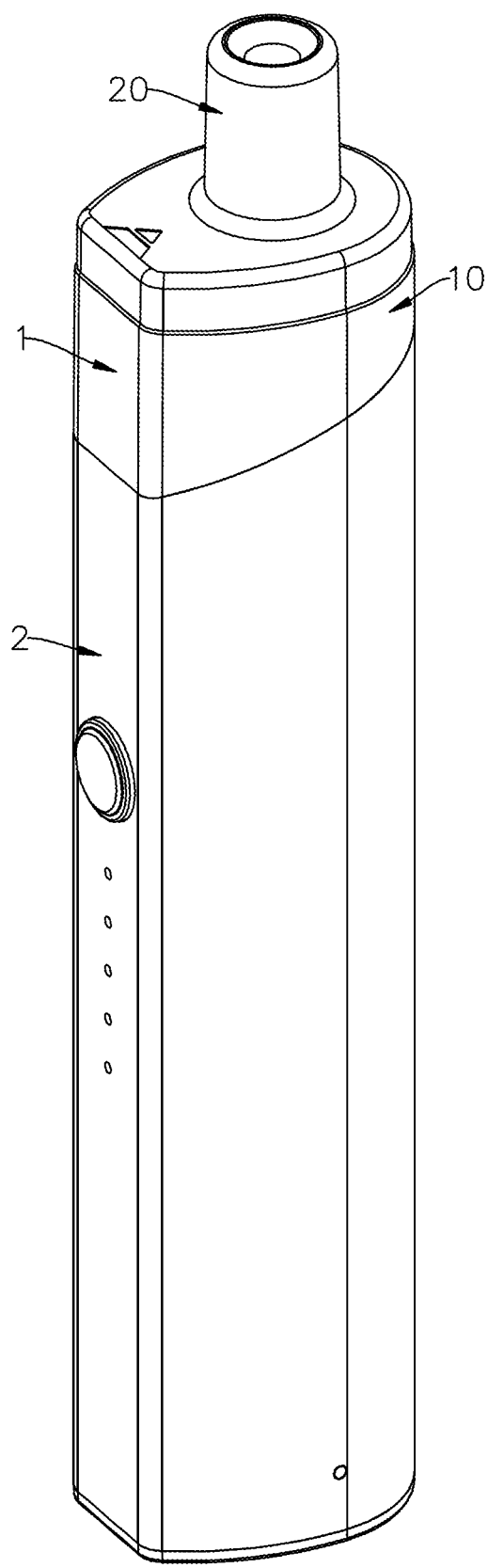
FIG. 1 is a three-dimensional structural view of an electronic atomizing device in some embodiments of the present disclosure.
Figure 2:
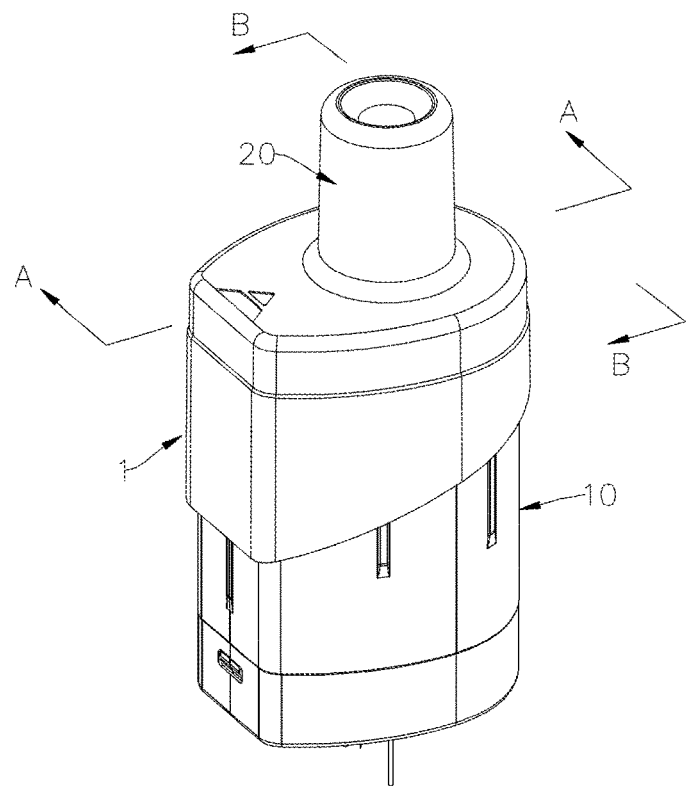
FIG. 2 is a three-dimensional structural view of an atomizer of the electronic atomizing device shown in FIG. 1 when a suction nozzle is in a fifth position.
Figure 3:
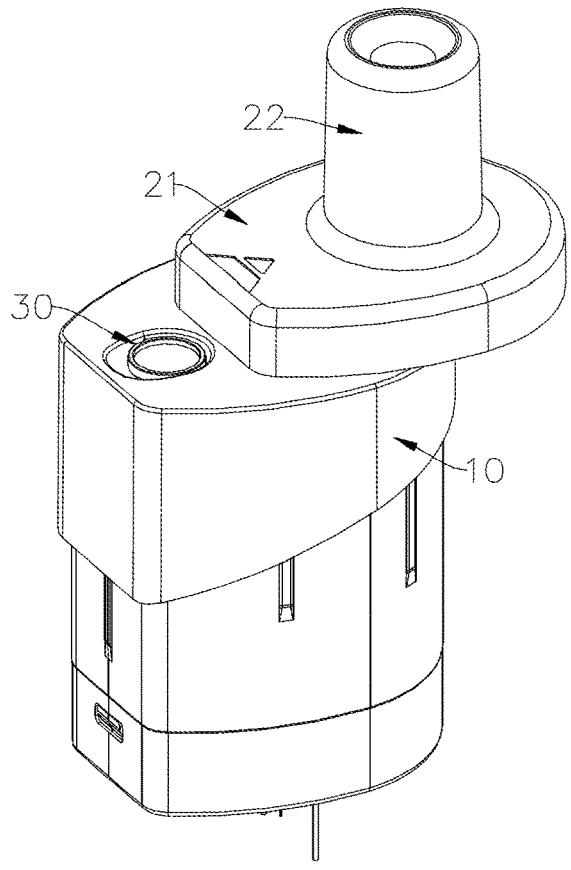
FIG. 3 is a three-dimensional structural view of the atomizer shown in FIG. 2 when the suction nozzle is in a sixth position.
Figure 4:
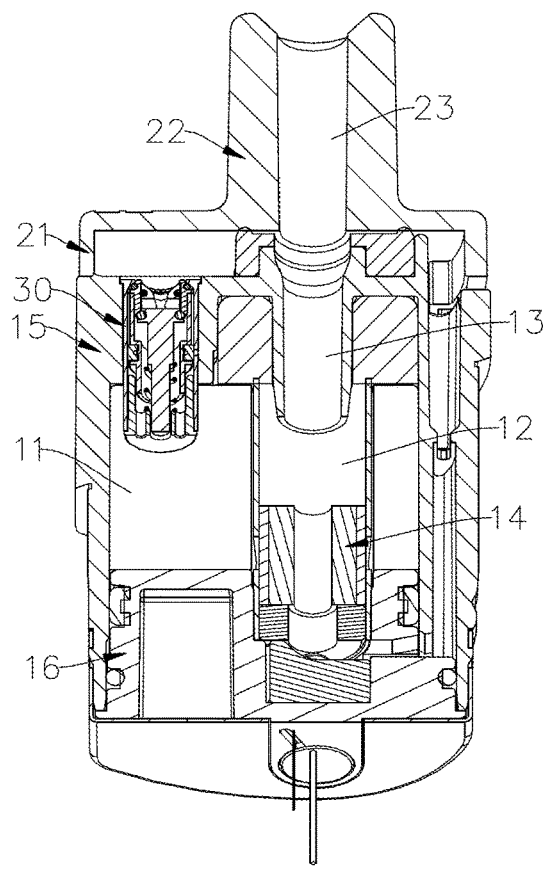
FIG. 4 is a sectional view A-A of the atomizer shown in FIG. 2.
Figure 5:
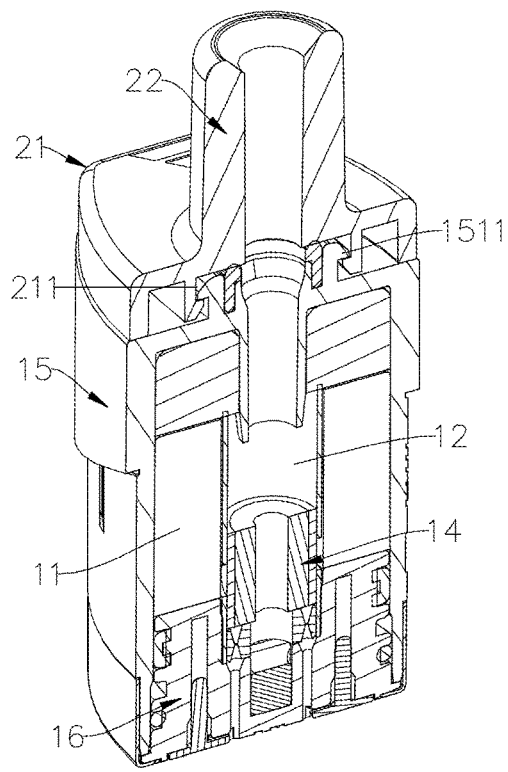
FIG. 5 is a sectional view B-B of the atomizer shown in FIG. 2.
Figure 6:
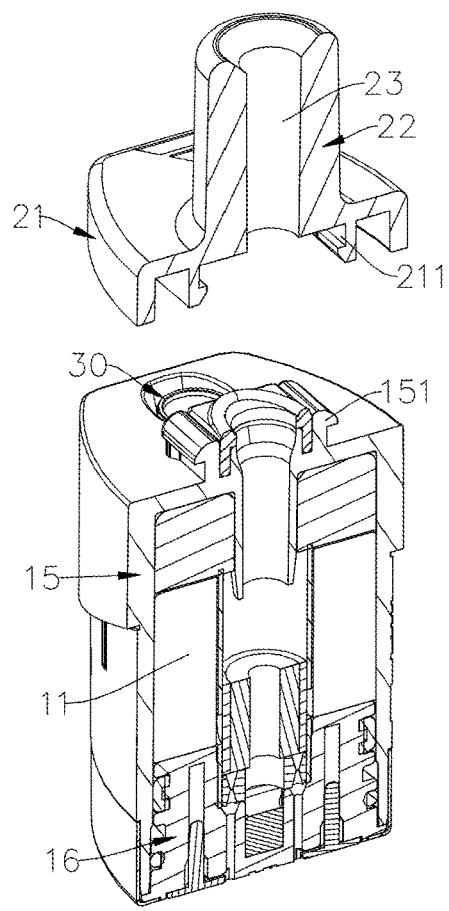
FIG. 6 is an exploded view of the atomizer shown in FIG. 5.
Figure 7:
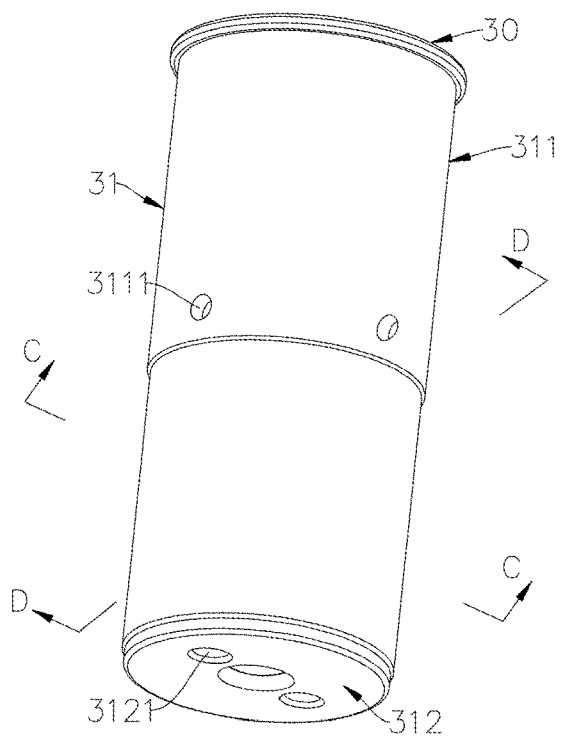
FIG. 7 is a three-dimensional view of a liquid injection structure according to a first embodiment of the present disclosure.
Figure 8:
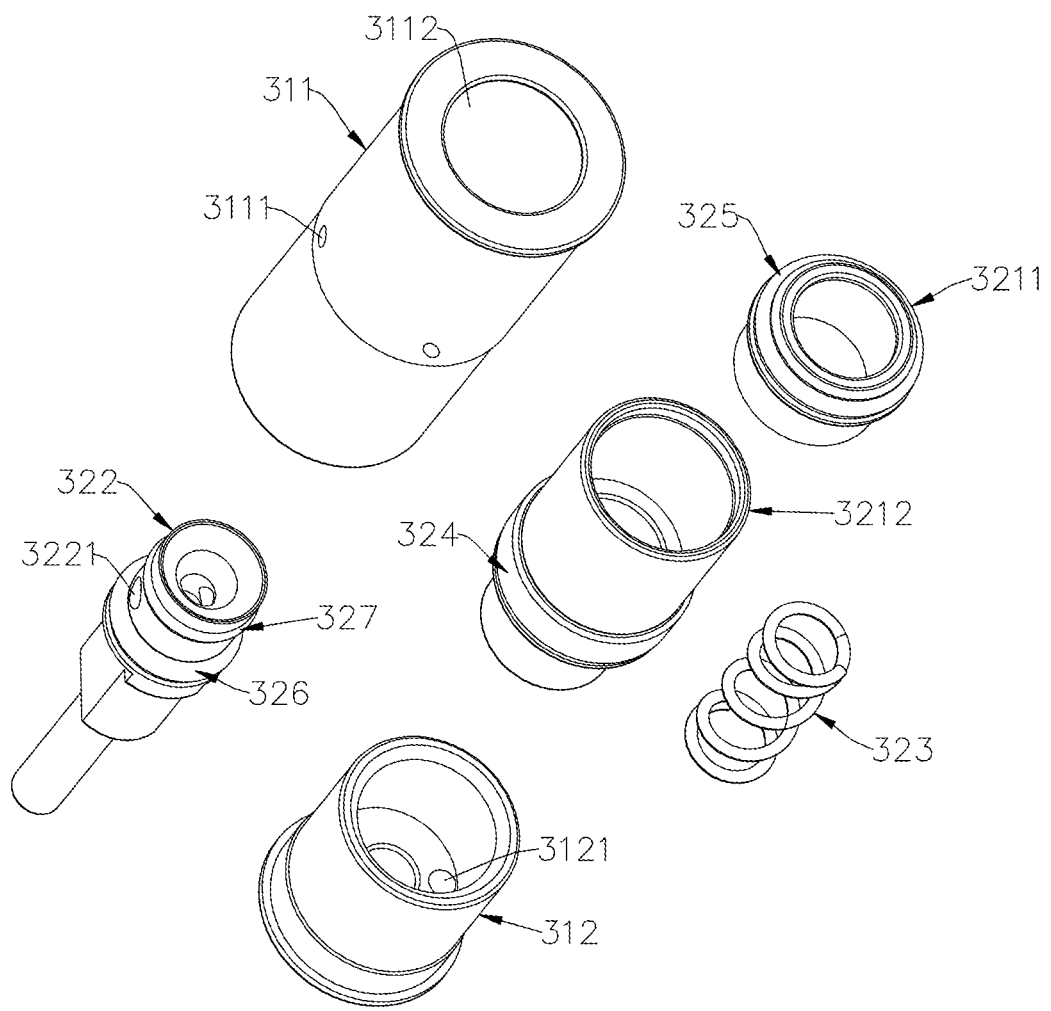
FIG. 8 is an exploded view of the liquid injection structure shown in FIG. 7.
Figure 9:
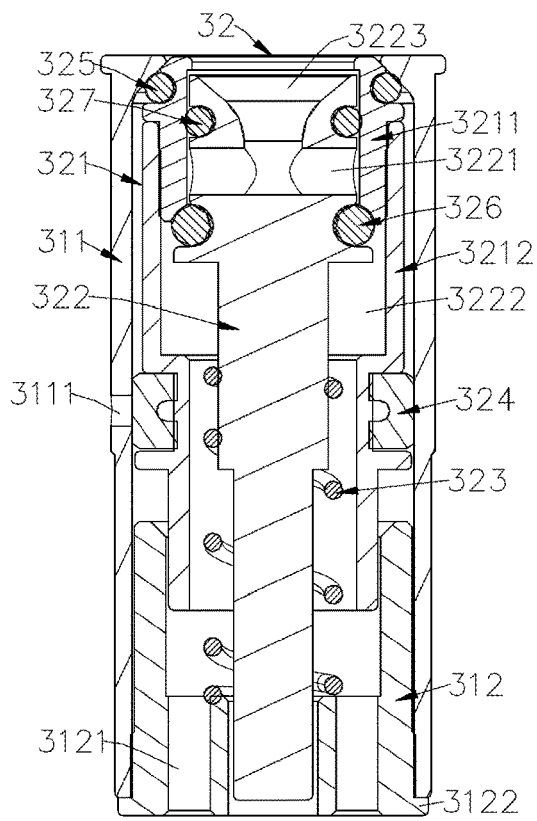
FIG. 9 is a sectional view C-C of the liquid injection structure shown in FIG. 7 when a liquid injection pipe is in a first position and a sleeve pipe is in a third position.

In order to describe the technical features, objectives and effects of the present disclosure more clearly, the specific implementations of the present disclosure are described in detail below with reference to the accompanying drawings.

FIGS. 1 to 6 show an electronic atomizing device in some embodiments of the present disclosure. The electronic atomizing device may be used to atomize a liquid medium such as a smoke liquid or a medicinal liquid, and may include a power supply device 2 and an atomizer 1 disposed on the power supply device 2. The power supply device 2 is electrically connected to the atomizer 1 to provide electrical energy for the atomizer 1. The atomizer 1 is used to receive a liquid medium such as a smoke liquid or a medicinal liquid and generate aerosol. The atomizer 1 may be disposed on the power supply device 2 such that a suction nozzle 20 of the atomizer 1 is exposed, which is convenient for a user to use.

The atomizer 1 in some embodiments may include an atomization unit 10, a liquid injection structure 30, and a suction nozzle 20 disposed at one end of the atomization unit 10. The atomization unit 10 is provided therein with a liquid storage cavity 11 for receiving a liquid medium such as a smoke liquid or a medicinal liquid. A liquid injection structure 30 may be disposed on a cavity wall forming the liquid storage cavity 11 to inject the liquid into the liquid storage cavity 11. The suction nozzle 20 in some embodiments may be disposed at an end of the atomizer 1 away from the power supply device 2. The suction nozzle 20 is provided with a first circulation passage 23 that extends axially therethrough. The atomization unit 10 is provided with a second circulation passage 13 fluidly communicated with the first circulation passage 23. The aerosol generated in the atomization unit 10 is able to flow from the second circulation passage 13 to the first circulation passage 23 and enter a user's mouth for the user to draw. The liquid injection structure 30 may be disposed at an end of the atomization unit 10 towards the suction nozzle 20, so that the suction nozzle 20 is able to shield the liquid injection structure 30 during a normal use of the atomizer 1 to prevent the liquid injection structure 30 from being easily opened.

The atomization unit 10 in some embodiments may include an atomization assembly 14, a first housing 15 and a second housing 16. The atomization unit 10 may be disposed on the power supply device 2 via the second housing 16. A liquid storage cavity 11 and an atomization cavity 12 are provided between the first housing 15 and the second housing 16. The atomization cavity 12 is in fluid communication with the second circulation passage 13. The atomization assembly 14 is disposed in the atomization cavity 12 and is in fluid connection with the liquid storage cavity 11 to heat and atomize the liquid medium in the liquid storage cavity 11. When the atomizer 1 and the power supply device 2 are assembled, the power supply device 2 supplies power to the atomization assembly 14 in the atomizer 1, and the atomization assembly 14 heats to heat and atomize the liquid medium, so as to generate aerosol for the user to draw.

The suction nozzle 20 and the liquid injection structure 30 can be disposed on the first housing 15. In some embodiments, the suction nozzle 20 is in sliding connection with the first housing 15, and the suction nozzle 20 is able to move back and forth between a fifth position and a sixth position relative to the first housing 15. When the suction nozzle 20 is in the fifth position relative to the first housing 15, the second circulation passage 13 is in fluid communication with the first circulation passage 23, and the liquid injection structure 30 is shielded by the suction nozzle 20, so that the atomizer 1 is able to be operated normally. When the suction nozzle 20 is in the sixth position relative to the first housing 15, the second circulation passage 13 is staggered with the first circulation passage 23, and the liquid injection structure 30 is exposed, so that the liquid is able to be injected into the liquid storage cavity 11 via the liquid injection structure 30.

The suction nozzle 20 and the first housing 15 are provided with a guide structure for guiding and positioning the sliding movement of the suction nozzle 20. The guide structure may include a first guide portion 211 provided on the suction nozzle 20 and a second guide portion 151 provided on the first housing 15.

In some embodiments, the suction nozzle 20 may include an annular suction nozzle holder 21 and a suction nozzle pipe 22 disposed on the suction nozzle holder 21. An inner hole of the suction nozzle pipe 22 defines the first circulation passage 23, and the suction nozzle 20 may be disposed on the first housing 15 via the suction nozzle holder 21. The first guide portion 211 and the second guide portion 151 may be a guide chute and a guide slider disposed on the suction nozzle holder 21 and the first housing 15, respectively. The guide chute and the guide slider extend along a sliding direction of the suction nozzle 20. The guide chute and the guide slider are snap-fitted with each other, so that the suction nozzle 20 maintains a connected state when sliding relative to the first housing 15. There may be two groups of the guide chutes and the guide sliders, which are respectively located on two opposite sides of the first circulation passage 23 to improve the sliding stability.

In this embodiment, a cross section of the guide slider is generally L-shaped, and a hook portion 1511 of the L-shaped guide slider is located in the guide chute and is in sliding connection with the guide chute. In other embodiments, the cross section of the guide slider may be in other shape such as a T shape. In some other embodiments, alternatively, the first guide portion 211 may be a guide slider disposed on the suction nozzle holder 21, and the second guide portion 151 may be a guide slider disposed on the first housing 15.

When the atomizer 1 in the present disclosure is in a normal use, the suction nozzle 20 is able to shield the liquid injection structure 30, so that the liquid injection structure 30 is not easily opened by accident, thereby avoiding a liquid leakage. When a liquid injection is needed, the suction nozzle holder 20 is pushed open to expose the liquid injection structure 30, enabling the liquid injection to be carried out quickly and conveniently. Understandably, in other embodiments, the suction nozzle 20 may be rotatably disposed at one end of the atomization unit 10, and be rotated to shield or expose the liquid injection structure 30. In another embodiments, the liquid injection structure 30 may be disposed at an end of the atomization unit 10 towards the power supply device 2, and when the atomizer 1 and the power supply device 2 are assembled, the liquid injection structure 30 is able to be concealed in a connection position between the atomizer 1 and the power supply device 2, making it difficult to be opened by accident.

Referring to FIGS. 7 to 12, the liquid injection structure 30 in a first embodiment may include an outer pipe 31 and a liquid injection assembly 32 disposed in the outer pipe 31. A side wall of the outer pipe 31 is provided with an exhaust port 3111 for discharging air in the liquid storage cavity 11. The air in the liquid storage cavity 11 is able to be discharged via the exhaust port 3111 while injecting liquid into the liquid storage cavity 11, to balance air pressure inside and outside the liquid storage cavity 11. The liquid injection assembly 32 includes a sleeve pipe 321, a liquid injection pipe 322 and an elastic member 323. The liquid injection pipe 322 is provided with a liquid injection port 3221. The liquid injection pipe 322 is axially disposed in the sleeve pipe 321 and is able to axially move back and forth relative to the sleeve pipe 321 between a first position adjacent to an outer end of the outer pipe 31 and a second position away from the outer end of the outer pipe 31. When the liquid injection pipe 322 is in the first position relative to the sleeve pipe 321, the sleeve pipe 321 seals the liquid injection port 3221, and when the liquid injection pipe 322 is in the second position relative to the sleeve pipe 321, the seal of the liquid injection port 3221 by the sleeve pipe 321 is released. The sleeve pipe 321 is axially disposed in the outer pipe 31 and is able to axially move back and forth relative to the outer pipe 31 between a third position adjacent to the outer end of the outer pipe 31 and a fourth position away from the outer end of the outer pipe 31. When the sleeve pipe 321 is in the third position relative to the outer pipe 31, the sleeve pipe 321 seals the exhaust port 3111, and when the sleeve pipe 321 is in the fourth position relative to the outer pipe 31, the seal of the exhaust port 3111 by the sleeve pipe 321 is released. The elastic member 323 is disposed between the liquid injection pipe 322 and the outer pipe 31 to elastically maintain the liquid injection pipe 322 in the first position and elastically maintain the sleeve pipe 321 in the third position.

The outer pipe 31 in some embodiments may include a first pipe body 311 and a base body 312 axially plugged at an inner end of the first pipe body 311 (an end towards the liquid storage cavity 11). The elastic member 323 may be sleeved outside the liquid injection pipe 322, and two ends of the elastic member 323 abut against the liquid injection pipe 322 and the base body 312, respectively. The base body 312 may be connected to the first pipe body 311 by riveting. An outer periphery of an inner end of the base body 312 may be radially provided with a first positioning flange 3122. The first positioning flange 3122 abuts against an inner end surface of the first pipe body 311 for mounting and positioning.

The exhaust port 3111 is defined on a side wall of the first pipe body 311. An outer end of the first pipe body 311 (an end away from the liquid storage cavity 11) is provided with an opening 3112. An exhaust cavity 3113 is provided between an inner wall of the first pipe body 311 and an outer wall of the liquid injection assembly 32. The exhaust port 3111, the exhaust cavity 3113 and the opening 3112 communicate fluidly in sequence to define an exhaust passage that fluidly connects the liquid storage cavity 11 with the outside to discharge the air in the liquid storage cavity 11. The base body 312 may be axially provided with a liquid inlet 3121 fluidly communicating with the liquid storage cavity 11. A liquid inlet cavity 3222 is defined between an outer wall of the liquid injection pipe 322 and inner walls of the sleeve pipe 321 and the base body 312. The liquid injection port 3221, the liquid inlet cavity 3222 and the liquid inlet 3121 fluidly communicate in sequence to define a liquid inlet passage that fluidly connects the liquid inlet 3221 with the liquid storage cavity 11 to inject the liquid into the liquid storage cavity 11.

The sleeve pipe 321 in some embodiments may include a third pipe body 3212 axially disposed in the first pipe body 311 and a second pipe body 3211 axially inserted at an outer end of the third pipe body 3212. The second pipe body 3211 may be connected to the third first pipe body 3212 by riveting. A first annular retaining ring 3213 may be provided outside the second pipe body 3211. The first annular retaining ring 3213 abuts against an outer end surface of the third pipe body 3212 for mounting and positioning.

In some embodiments, an outer end of the second pipe body 3211 may extend out of the third pipe body 3212. An inner periphery of the outer end of the first pipe body 311 is radially provided with a second annular retaining ring 3114, and an inner hole of the second annular retaining ring 3114 defines the opening 3112. The outer end of the second pipe body 3211 is movably abutted against the second annular retaining ring 3114 to open or close the opening 3112.

The liquid injection pipe 322 is axially disposed in the second pipe body 3211. An inner periphery of the outer end of the second pipe body 3211 is radially provided with a third annular retaining ring 3215. An outer end surface of the liquid injection pipe 322 movably abuts against the third annular retaining ring 3215. When the liquid injection pipe 322 is in the first position relative to the sleeve pipe 321, an axial position of the liquid injection port 3221 correspondingly on the liquid injection pipe 322 is in an axial section where the second pipe body 3211 is located, such that the second pipe body 3211 seals the liquid injection port 3221. When the liquid injection pipe 322 is in the second position relative to the sleeve pipe 321, the axial position of the liquid injection port 3221 correspondingly on the liquid injection pipe 322 is out of the axial section where the second pipe body 3211 is located, and the seal of the liquid injection port 3221 by the second pipe body 3211 is released.

The liquid injection assembly 32 in some embodiments may further include a first sealing member 324, a second sealing member 325 and a third sealing member 326. The first sealing member 324 is disposed on an outer wall of the third pipe body 3212 to isolate the exhaust port 3111 from the exhaust cavity 3113. The first sealing member 324 may have an annular shape, and is sleeved outside the third pipe body 3212. A first clamping slot 3241 for disposing the first sealing member 324 is provided on an outer side of the third pipe body 3212. When the sleeve pipe 321 is in the third position relative to the outer pipe 31, the first sealing member 324 is correspondingly located at the exhaust port 3111 to seal the exhaust port 3111, so that the exhaust port 3111 is isolated from the exhaust cavity 3113. When the sleeve pipe 321 moves downward relative to the outer pipe 31 to the fourth position, the first sealing member 324 moves downward to stagger with the exhaust port 3111, so that the exhaust port 3111 communicates fluidly with the exhaust cavity 3113.

The second sealing member 325 is fitted at the opening 3112, and may be disposed on an outer wall of the second pipe body 3211, to seal the opening 3112 and isolate the exhaust cavity 3113 from the opening 3112. The first sealing member 324 and the second sealing member 325 respectively seal the bottom and the top of the exhaust passage, thereby further improving the sealing performance. In addition, in a non-injection state, the second sealing member 325 is able to maintain a seal between the outer end of the outer pipe 31 and the liquid injection assembly 32 to avoid leakage of the liquid medium, thereby improving the user experience.

The second sealing member 325 may have an O shape, and is sleeved outside the second pipe body 3211. A second clamping slot 3251 for disposing the second sealing member 325 is provided on an outer side of the second pipe body 3211. The second clamping slot 3251 may be defined on the first annular retaining ring 3213, or alternatively be independently provided. When the sleeve pipe 321 is in the third position relative to the outer pipe 31, the second sealing member 325 is in a sealing fit with the second annular retaining ring 3114 to seal the opening 3112, so that the opening 3112 is isolated from the exhaust cavity 3113. When the sleeve pipe 321 moves downward relative to the outer pipe 31 to the fourth position, the second sealing member 325 moves downward to stagger with the second annular retaining ring 3114, so that the opening 3112 communicates fluidly with the exhaust cavity 3113. A side surface of the second annular retaining ring 3114 towards the second sealing member 325 may have an inclined surface, to facilitate manufacture and improve the sealing effect.

The third sealing member 326 is disposed on an outer wall of the liquid injection pipe 322 to isolate the liquid injection port 3221 from the liquid inlet 3121. The third sealing member 326 may have an O shape, and is sleeved outside the liquid injection pipe 322. A third clamping slot 3261 for disposing the third sealing member 326 is provided on an outer side of the liquid injection pipe 322. The third sealing member 326 is in a sealing fit with an inner end surface of the second pipe body 3211. When the liquid injection pipe 322 is in the first position relative to the sleeve pipe 321, the third sealing member 326 is in a sealing fit with the inner end surface of the second pipe body 3211 to isolate the liquid injection port 3221 from the liquid inlet 3121. When the liquid injection pipe 322 moves downward relative to the sleeve pipe 321 to the second position, the third sealing member 326 moves downward to stagger with the inner end surface of the second pipe body 3211, so that the liquid injection port 3221 fluidly communicates with the liquid inlet 3121.

The liquid injection assembly 32 in some embodiments may further include a fourth sealing member 327 disposed on an outer wall of the liquid injection pipe 322. The fourth sealing member 327 and the third sealing member 326 are respectively locate d on two opposite sides of the liquid injection port 3221 to seal the top and the bottom of the liquid injection port 3221 respectively, so as to minimize the liquid medium remaining in the liquid injection port 3221 after the liquid injection is finished, making cleaning easy. The fourth sealing member 327 may have an O shape, and is sleeved outside the liquid injection pipe 322. A fourth clamping slot 3271 for disposing the fourth sealing member 327 is provided on the outer side of the liquid injection pipe 322.

The third pipe body 3212 in some embodiments may include a first pipe section 3216 and a second pipe section 3217 disposed at an inner end of the first pipe section 3216. The second pipe body 3211 is disposed in the first pipe section 3216. An outer diameter and an inner diameter of the first pipe section 3216 are respectively larger than those of the second pipe section 3217, and a second positioning flange 3218 is formed at a junction between the first pipe section 3216 and the second pipe section 3217. An inner end of the second pipe section 3217 is able to extend into the base body 312. A third positioning flange 3219 may be provided outside the second pipe section 3217. An outer diameter of the second positioning flange 3219 is larger than an inner diameter of an outer end of the base body 312, so that the second positioning flange 3219 is able to be movably abutted on an outer end surface of the base body 312. The first clamping slot 3241 may be defined between the second positioning flange 3218 and the third positioning flange 3219, or alternatively be independently provided.

In some embodiments, a fourth positioning flange 3224 and a fifth positioning flange 3225 are further provided outside the liquid injection pipe 322 respectively. The fourth positioning flange 3224 is axially movably fitted in the first pipe section 3216, and an outer dimension of the fourth positioning flange 3224 is larger than inner diameters of the second pipe section 3217 and the second pipe body 3211 respectively. When the liquid injection pipe 322 is in the first position relative to the sleeve pipe 321, an outer end surface of the fourth positioning flange 3224 abuts against an inner end surface of the second pipe body 3211. When the liquid injection pipe 322 is in the second position relative to the sleeve pipe 321, an inner end surface of the fourth positioning flange 3224 abuts against the second positioning flange 3218. The fifth positioning flange 3225 is axially movably fitted in the second pipe section 3217, and two ends of the elastic member 323 may abut against the fifth positioning flange 3225 and the base body 312, respectively.

Figure 10:
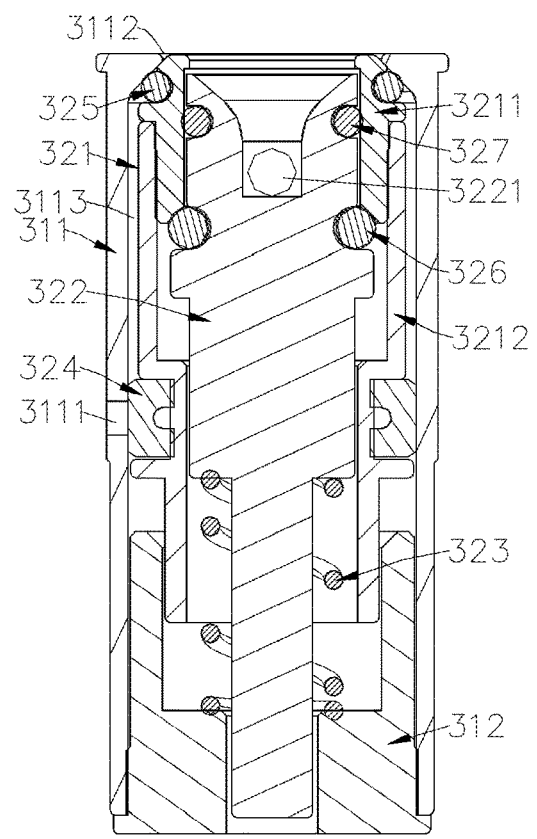
FIG. 10 is a sectional view D-D of the liquid injection structure shown in FIG. 7 when the liquid injection pipe is in the first position and the sleeve pipe is in the third position.
Figure 11:
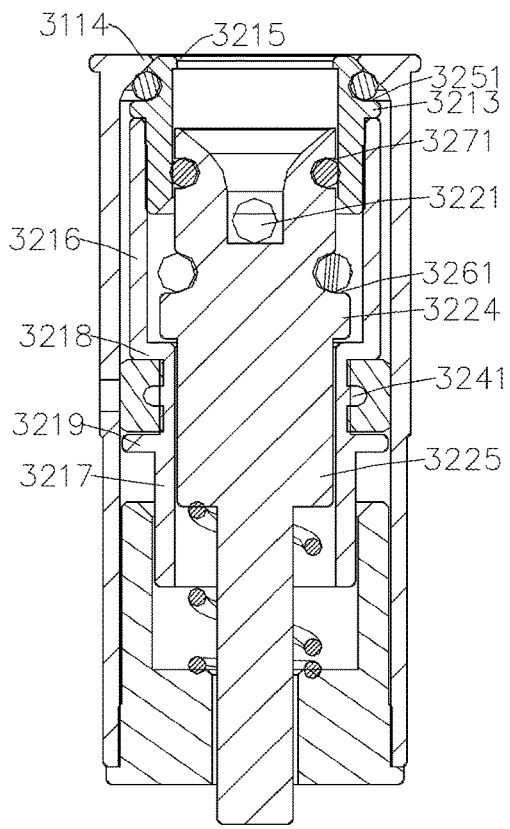
FIG. 11 is a sectional view of the liquid injection structure shown in FIG. 10 when the liquid injection pipe is in a second position and the sleeve pipe is in the third position.
Figure 12:
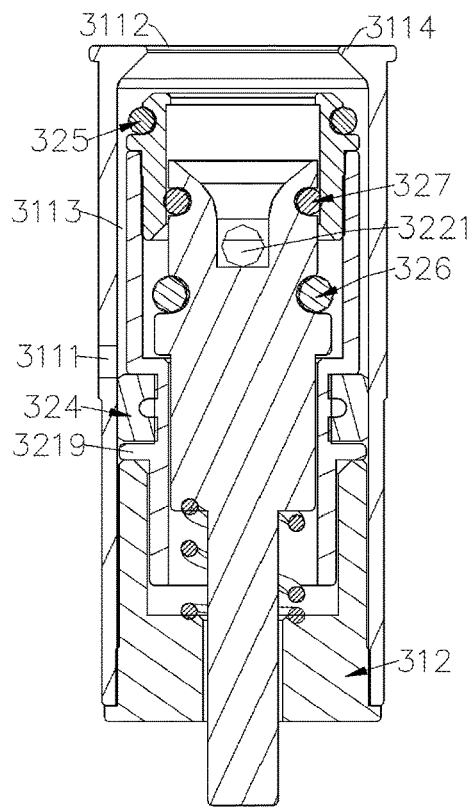
FIG. 12 is a sectional view of the liquid injection structure shown in FIG. 10 when the liquid injection pipe is in the second position and the sleeve pipe is in a fourth position.
Figure 13:
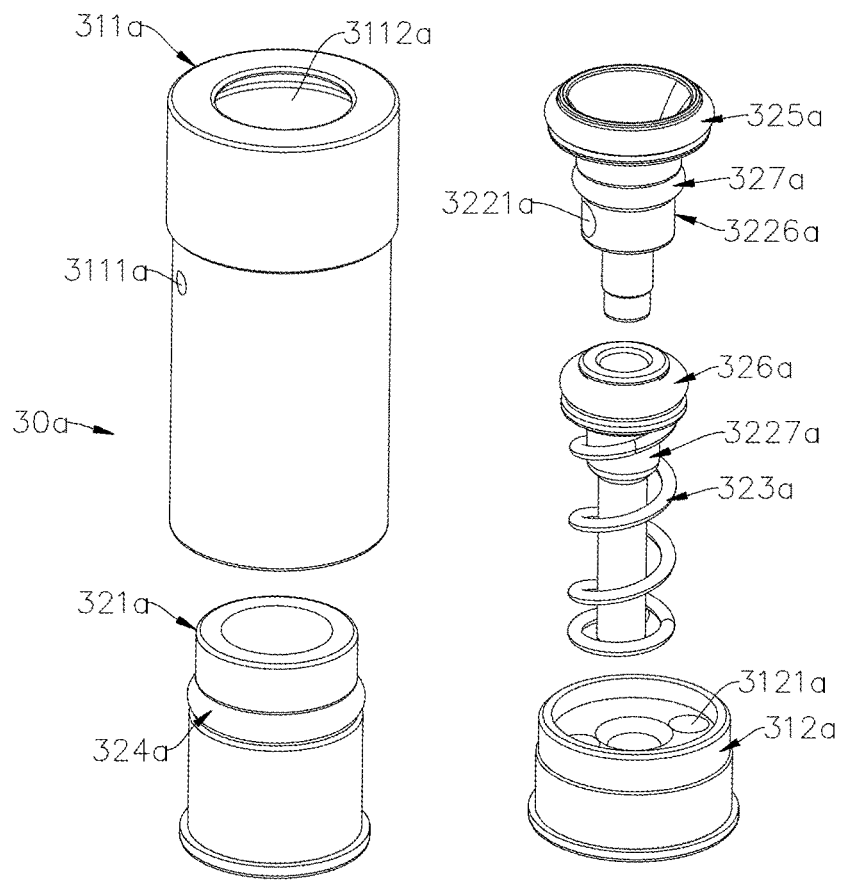
FIG. 13 is an exploded view of a liquid injection structure according to a second embodiment of the present disclosure.

In some embodiments, a friction force between the liquid injection pipe 322 and the sleeve pipe 321 is less than a friction force between the sleeve pipe 321 and the outer pipe 31. An inner hole at an outer end of the liquid injection pipe 322 may be flared to facilitate connection and injection. As shown in FIG. 10, when no liquid injection is performed, the liquid injection pipe 322 is in the first position relative to the sleeve pipe 321, and the sleeve pipe 321 is in the third position relative to the outer pipe 31; at this time, the liquid injection passage and the exhaust passage are closed, and two ends of the liquid injection pipe 322 and the sleeve pipe 321 are retracted into the outer pipe 31. When a liquid injection needs to be performed, the liquid injection pipe 322 is pressed down, so that the liquid injection pipe 322 moves downward from the first position to the second position relative to the sleeve pipe 321; at this time, the fourth positioning flange 3224 on the liquid injection pipe 322 abuts against the second positioning flange 3218 on the sleeve pipe 321, and the third sealing member 326 moves downward to stagger with the inner end surface of the second pipe body 3211, so that the liquid injection port 3221 fluidly communicates with the liquid inlet 3121 to open the liquid injection passage, as shown in FIG. 11. Continuing to press the liquid injection pipe 322 down, the liquid injection pipe 322 will drive the sleeve pipe 321 to move downward together to enable the sleeve pipe 321 to move downward relative to the outer pipe 31 from the third position to the fourth position; at this time the third positioning flange 3219 on the sleeve pipe 321 abuts against the outer end surface of the base body 312, and the first sealing member 324 moves downward to stagger with the exhaust port 3111, so that the exhaust port 3111 fluidly communicates with the exhaust cavity 3113. The second sealing member 325 moves downward to stagger with the opening 3112, so that the exhaust cavity 3113 fluidly communicates with the opening 3112, and the exhaust passage is opened, as shown in FIG. 12. After the liquid injection is finished, a pressing force applied on the liquid injection pipe 322 is removed, the liquid injection pipe 322 returns from the second position to the first position under the action of the elastic member 323, and the liquid injection passage is closed. Then, the liquid injection pipe 322 continues to drive the sleeve pipe 321 to move and enables the sleeve pipe 321 to return from the fourth position to the third position, so that the exhaust passage is closed.

FIGS. 13 to 16 show a liquid injection structure 30a in a second embodiment of the present disclosure. In this embodiment, two ends of a liquid injection pipe 322a extend out of a sleeve pipe 321a respectively. The liquid injection pipe 322a may include a fourth pipe body 3226a and a fifth pipe body 3227a sleeved outside an inner end of the fourth pipe body 3226a. A liquid injection port 3221a may be defined on the fourth pipe body 3226a. The fourth pipe body 3226a may be connected to the fifth pipe body 3227a by riveting. A sixth positioning flange 3224a and a seventh positioning flange 3228a may be provided outside the fourth pipe body 3226a respectively. The seventh positioning flange 3228a abuts against an outer end surface of the fifth pipe body 3227a for mounting and positioning. An outer diameter of the sixth positioning flange 3224a is larger than an inner diameter of an outer end of the sleeve pipe 321a, and the sixth positioning flange 3224a movably abuts against an outer end surface of the sleeve pipe 321a.

Similar to the first embodiment, an outer pipe 31a in this embodiment includes a first pipe body 311a and a base body 312a axially plugged at an inner end of the first pipe body 311a, and the base body 312a may be axially provided with a liquid inlet 3121a fluidly communicating with the liquid storage cavity 11. An inner periphery of an outer end of the first pipe body 311a is radially provided with a second annular retaining ring 3114a, and an inner hole of the second annular retaining ring 3114a defines an opening 3112a. The sixth positioning flange 3224a movably abuts against the second annular retaining ring 3114a to open or close the opening 3112a. When the liquid injection pipe 322a is in a first position relative to the sleeve pipe 321a, an outer end surface of the sixth positioning flange 3224a abuts against the second annular retaining ring 3114a, and an inner end surface of the sixth positioning flange 3224a is spaced from an outer end surface of the sleeve pipe 321a. When the liquid injection pipe 322a is in a second position relative to the sleeve pipe 321a, the outer end surface of the sixth positioning flange 3224a is spaced from the second annular retaining ring 3114a, and the inner end surface of the sixth positioning flange 3224a abuts against the outer end surface of the sleeve pipe 321a. An elastic member 323a is sleeved outside the liquid injection pipe 322a, and two ends of the elastic member 323a abut against the liquid injection pipe 322a and the base body 312a, respectively.

An exhaust port 3111a is defined on a side wall of the first pipe body 311a. An exhaust cavity 3113a is defined between an inner wall of the first pipe body 311a and an outer wall of a liquid injection assembly 32a. The exhaust port 3111a, the exhaust cavity 3113a and the opening 3112a communicate in sequence fluidly to form an exhaust passage that fluidly connects the liquid storage cavity 11 with the outside. A liquid inlet cavity 3222a is defined between an outer wall of the liquid injection pipe 322a and inner walls of the sleeve pipe 321a and the base body 312a. The liquid injection port 3221a, the liquid inlet cavity 3222a and the liquid inlet 3121a fluidly communicate in sequence to form a liquid inlet passage that fluidly connects the liquid inlet 3221a with the liquid storage cavity 11.

In some embodiments, the fifth pipe body 3227a may be externally provided with an eighth positioning flange 3225a for the elastic member 323a to abut against. Two ends of the elastic member 323a may respectively abut against the eighth positioning flange 3225a and the base body 312a, so as to provide an elastic force for returning.

Similar to the first embodiment, the liquid injection assembly 32a in this embodiment may include a first sealing member 324a and a second sealing member 325a for respectively sealing the bottom and the top of the exhaust passage, and a third sealing member 326a and a fourth sealing member 327a for respectively sealing the bottom and the top of the liquid injection port 3221a.

The first sealing member 324a is disposed on an outer wall of the sleeve pipe 321a to isolate the exhaust port 3111a from the exhaust cavity 3113a. The first sealing member 324a may have an O shape, and is sleeved outside the sleeve pipe 321a. A first clamping slot 3241a for disposing the first sealing member 324a is provided on an outer side of the sleeve pipe 321a. When the sleeve pipe 321a is in a third position relative to the outer pipe 31a, the first sealing member 324a is located above the exhaust port 3111a to seal the exhaust port 3111a, so that the exhaust port 3111a is isolated from the exhaust cavity 3113a. When the sleeve pipe 321a moves downward relative to the outer pipe 31a to a fourth position, the first sealing member 324a moves downward to below the exhaust port 3111a, so that the exhaust port 3111a fluidly communicates with the exhaust cavity 3113a.

The second sealing member 325a is disposed on an outer wall of the fourth pipe body 3226a to seal the opening 3112a, so as to isolate the exhaust cavity 3113a from the opening 3112a. In a non-injection state, the second sealing member 325a is able to maintain a seal between an outer end of the outer pipe 31a and the liquid injection assembly 32a to avoid leakage of the liquid medium, thereby improving the user experience. The second sealing member 325a may have an O shape, and is sleeved outside the fourth pipe body 3226a. A second clamping slot 3251a for disposing the second sealing member 325a is provided on an outer side of the fourth pipe body 3226a. The second clamping slot 3251a may be defined on the sixth positioning flange 3224a, or alternatively be independently provided. When the liquid injection pipe 322a is in the first position relative to the sleeve pipe 321a, the second sealing member 325a is in a sealing fit with the second annular retaining ring 3114a to seal the opening 3112a, so that the opening 3112a is isolated from the exhaust cavity 3113a. When the liquid injection pipe 322a moves downward relative to the sleeve pipe 321a to the second position, the second sealing member 325a moves downward to stagger with the second annular retaining ring 3114a, so that the opening 3112a fluidly communicates with the exhaust cavity 3113a. A side surface of the second annular retaining ring 3114a towards the second sealing member 325a may be an inclined surface, to improve the sealing effect.

The third sealing member 326a is disposed on an outer wall of the fifth pipe body 3227a to isolate the liquid injection port 3221a from the liquid inlet 3121a. The third sealing member 326a may have an O shape, and is sleeved outside the fifth pipe body 3227a. A second clamping slot 3261a for disposing the third sealing member 326a is provided on an outer side of the fifth pipe body 3227a. The third clamping slot 3261a may be defined on the eighth positioning flange 3225a, or alternatively be independently provided.

The sleeve pipe 321a in some embodiments may include a third pipe section 3216a and a fourth pipe section 3217a disposed at an inner end of the third pipe section 3216a. An inner diameter of the fourth pipe section 3217a is larger than an inner diameter of the third pipe section 3216a. A fourth annular retaining ring 321a is formed at a junction between an inner hole of the third pipe section 3216a and an inner hole of the fourth pipe section 3217a. The fourth annular retaining ring 3211a may be disposed corresponding to the first clamping slot 3241a in an axial position, or alternatively be staggered with the first clamping slot 3241a in the axial position. The third sealing member 326a is in a sealing fit with the fourth annular retaining ring 3211a. When the liquid injection pipe 322a is in the first position relative to the sleeve pipe 321a, the third sealing member 326a is in a sealing fit with the fourth annular retaining ring 3211a to isolate the liquid injection port 3221a from the liquid inlet 3121a. When the liquid injection pipe 322a moves downward relative to the sleeve pipe 321a to the second position, the third sealing member 326a moves downward to stagger with the fourth annular retaining ring 3211a, so that the liquid injection port 3221a fluidly communicates with the liquid inlet 3121a. An outer diameter of the third pipe section 3216a may be less than an outer diameter of the fourth pipe section 3217a, so that a sufficient space is defined between the third pipe section 3216a and a side wall of the first pipe body 311a to discharge the air.

The fourth sealing member 327a is disposed on the outer wall of the fourth pipe body 3226a, to avoid the backflow of the liquid medium in the liquid inlet cavity 3222a, and to minimize the liquid medium remaining in the pipe after injection. The fourth sealing member 327a may have an O shape, and is sleeved outside the fourth pipe body 3226a. A second clamping slot 3271a for disposing the fourth sealing member 327a is provided on the outer side of the fourth pipe body 3226a. When the liquid injection pipe 322a is in the first position relative to the sleeve pipe 321a, the fourth sealing member 327a is in a sealing fit with an opening of the outer end of the sleeve pipe 321a. When the liquid injection pipe 322a moves downward relative to the sleeve pipe 321a to the second position, the fourth sealing member 327a moves downward to abut against the fourth annular retaining ring 3211a. Two side surfaces of the fourth annular retaining ring 3211a towards the third sealing member 326a and the fourth sealing member 327a respectively may be inclined surfaces, to facilitate manufacture and improve the sealing effect.

In some embodiments, a ninth positioning flange 3116a may be provided radially inside the first pipe body 311a, and a tenth positioning flange 3229a may be provided radially at an outer periphery of an inner end of the sleeve pipe 321a. An outer end surface of the tenth positioning flange 3229a movably abuts against the ninth positioning flange 3116a, so that the sleeve pipe 321a is able to be elastically maintained in the third position by the elastic member 323a.

Figure 14:
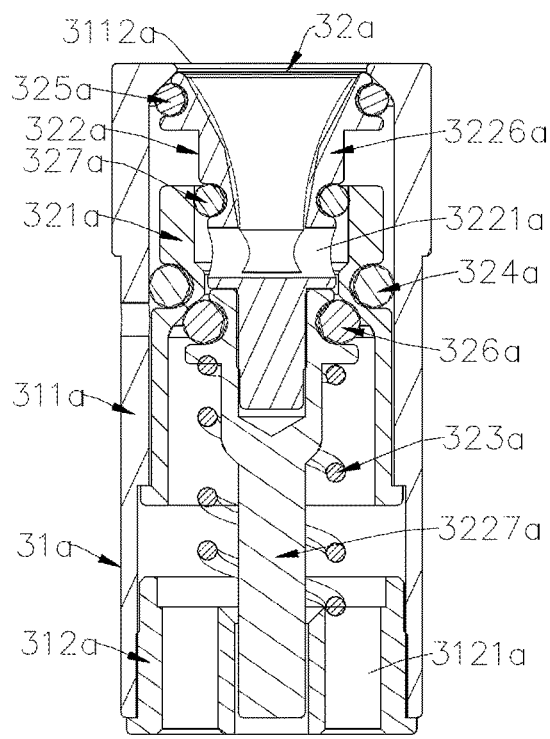
FIG. 14 is a sectional view of the liquid injection structure shown in FIG. 13 when a liquid injection pipe is in a first position and a sleeve pipe is in a third position.
Figure 15:
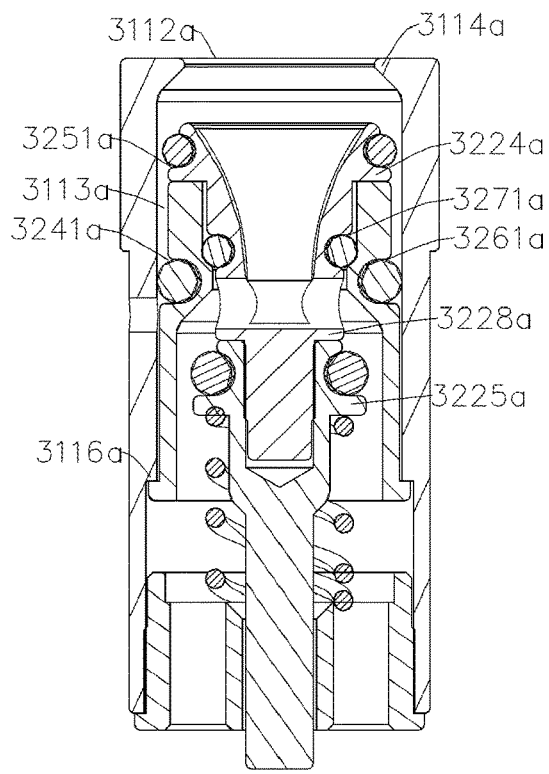
FIG. 15 is a sectional view of the liquid injection structure shown in FIG. 14 when the liquid injection pipe is in a second position and the sleeve pipe is in the third position.
Figure 16:
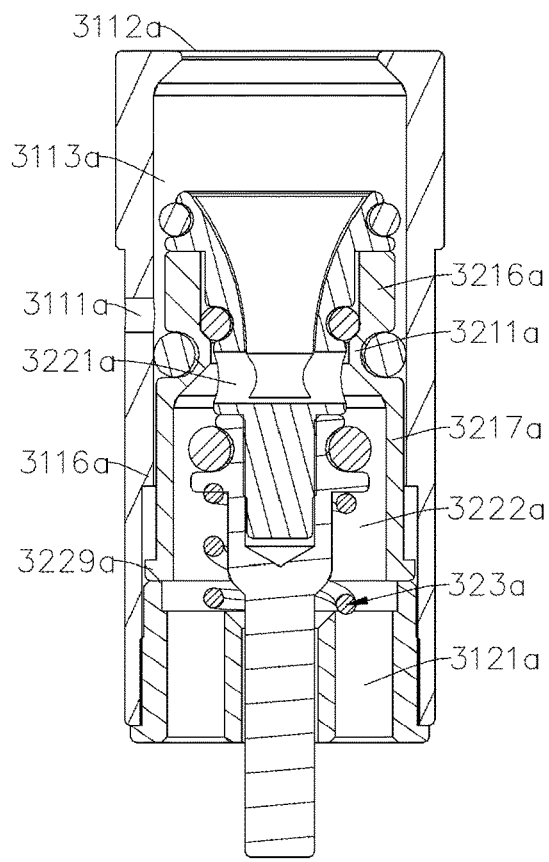
FIG. 16 is a sectional view of the liquid injection structure shown in FIG. 14 when the liquid injection pipe is in the second position and the sleeve pipe is in a fourth position.

In some embodiments, a friction force between the liquid injection pipe 322a and the sleeve pipe 321a is less than a friction force between the sleeve pipe 321a and the outer pipe 31a. An inner hole at an outer end of the liquid injection pipe 322a may be flared to facilitate connection and injection. As shown in FIG. 14, when no liquid injection is needed, the liquid injection pipe 322a is in the first position relative to the sleeve pipe 321a, and the sleeve pipe 321a is in the third position relative to the outer pipe 31a; at this time, the liquid injection passage and the exhaust passage are closed, and two ends of the liquid injection pipe 322a and the sleeve pipe 321a are retracted into the outer pipe 31a. As shown in FIG. 15, when a liquid injection needs to be performed, the liquid injection pipe 322a is pressed down, the liquid injection pipe 322a moves downward from the first position to the second position relative to the sleeve pipe 321a; at this time, the sixth positioning flange 3224a on the liquid injection pipe 322a abuts against the outer end surface of the sleeve pipe 321a, the third sealing member 326a moves downward to stagger with the fourth annular retaining ring 321a on the sleeve pipe 321a, so that the liquid injection port 3221a fluidly communicates with the liquid inlet 3121a to open the liquid injection passage, and the second sealing member 325a moves downward to stagger with the opening 3112a to enable the exhaust cavity 3113a to be fluidly communicated with the opening 3112a. Continuing to press the liquid injection pipe 322a, the liquid injection pipe 322a drives the sleeve pipe 321a to move downward together and enables the sleeve pipe 321a to move downward relative to the outer pipe 31a from the third position to the fourth position; at this time, an inner end surface of the sleeve pipe 321a abuts against an outer end surface of the base body 312a, and the first sealing member 324a moves downward to below the exhaust port 3111a, so that the exhaust port 3111a fluidly communicates with the exhaust cavity 3113a to open the exhaust passage, as shown in FIG. 16. After the liquid injection is finished, a pressing force on the liquid injection pipe 322a is removed, the liquid injection pipe 322a returns from the second position to the first position under the action of the elastic member 323a, the liquid injection passage is closed, and the opening 3112a is sealed. Then, the liquid injection pipe 322a continues to drive the sleeve pipe 321a to move and enables the sleeve pipe 321a to return from the fourth position to the third position, so that the exhaust passage is closed.

Figure 17:
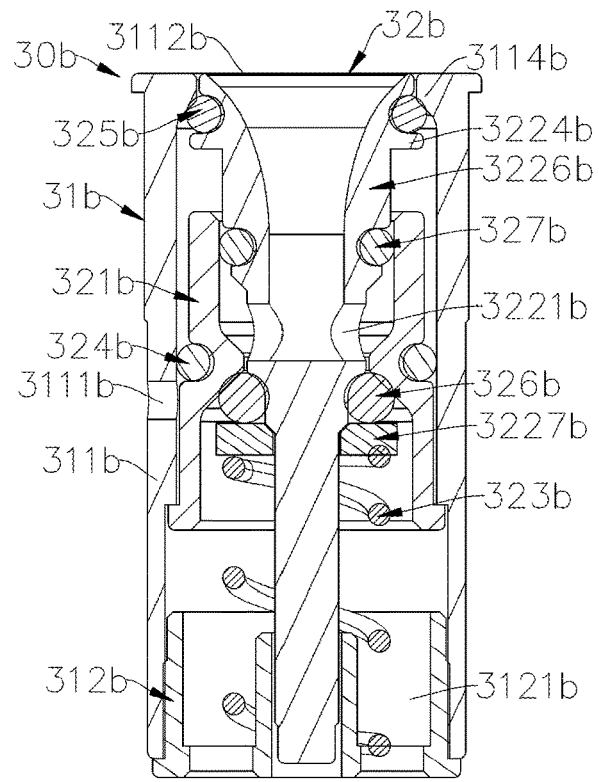
FIG. 17 is a sectional view of a liquid injection structure according to a third embodiment of the present disclosure when a liquid injection pipe is in a first position and a sleeve pipe is in a third position.
Figure 18:
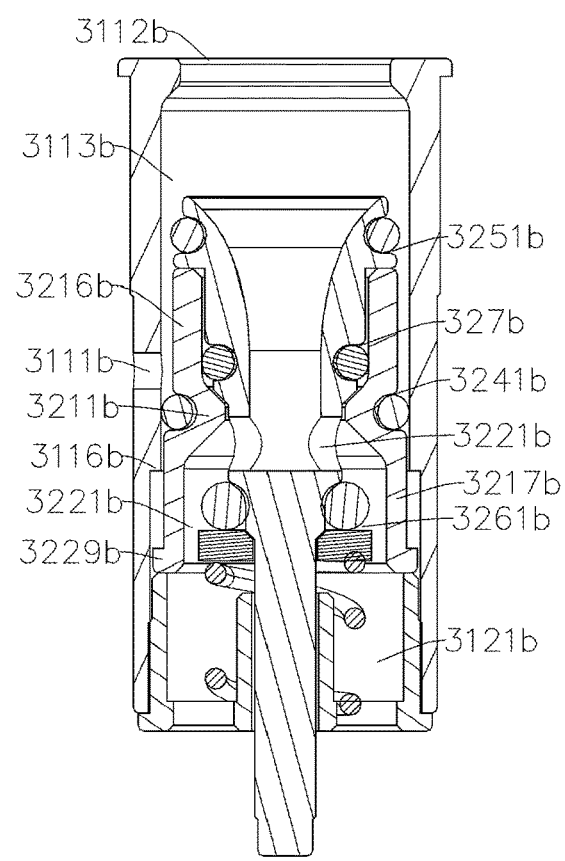
FIG. 18 is a sectional view of the liquid injection structure shown in FIG. 17 when the liquid injection pipe is in a second position and the sleeve pipe is in a fourth position.

FIGS. 17 and 18 show a liquid injection structure 30b in a third embodiment of the present disclosure. Compared with the second embodiment, a liquid injection pipe 322b in this embodiment may include a main body 3226b and a positioning member 3227b detachably sleeved outside the main body 3226b. The main body 3226b extends in a sleeve pipe 321b, and two ends of the main body 3226b extend out of the sleeve pipe 321b respectively. A sixth positioning flange 3224b may be provided outside the main body 3226b, and the sixth positioning flange 3224b movably abuts against an outer end surface of the sleeve pipe 321b. The positioning member 3227b in some embodiments may be a gasket, for mounting an elastic member 323b and a third sealing member 326b.

Similar to the second embodiment, an outer pipe 31b in this embodiment includes a first pipe body 311b and a base body 312b axially plugged at an inner end of the first pipe body 311b, and the base body 312b may be axially provided with a liquid inlet 3121b fluidly communicating with the liquid storage cavity 11. An inner periphery of an outer end of the first pipe body 311b is radially provided with a second annular retaining ring 3114b, and an inner hole of the second annular retaining ring 3114b defines an opening 3112b. The six positioning flange 3224b movably abuts against the second annular retaining ring 3114b to open or close the opening 3112b. The elastic member 323b is sleeved outside the liquid injection pipe 322b, and two ends of the elastic member 323b abut against the positioning member 3227b and the base body 312b, respectively.

An exhaust port 3111b is defined on a side wall of the first pipe body 311b. An exhaust cavity 3113b is defined between an inner wall of the first pipe body 311b and an outer wall of a liquid injection assembly 32b. The exhaust port 3111b, the exhaust cavity 3113b and the opening 3112b fluidly communicate in sequence to form an exhaust passage that fluidly connects the liquid storage cavity 11 with the outside. A liquid inlet cavity 3222b is defined between an outer wall of the liquid injection pipe 322b and inner walls of the sleeve pipe 321b and the base body 312b. The liquid injection port 3221b, the liquid inlet cavity 3222b and the liquid inlet 3121b fluidly communicate in sequence to form a liquid inlet passage that fluidly connects the liquid inlet 3221b with the liquid storage cavity 11.

Similar to the second embodiment, the liquid injection assembly 32b in this embodiment may include a first sealing member 324b and a second sealing member 325b for respectively sealing the bottom and the top of the exhaust passage, and a third sealing member 326b and a fourth sealing member 327b for respectively sealing the bottom and the top of the liquid injection port 3221b.

The first sealing member 324 is disposed on an outer wall of the sleeve pipe 321b to isolate the exhaust port 3111b from the exhaust cavity 3113b. The first sealing member 324b may have an O shape, and is sleeved outside the sleeve pipe 321b. A first clamping slot 3241b for disposing the first sealing member 324b is provided on an outer side of the sleeve pipe 321b. When the sleeve pipe 321b is in a third position relative to the outer pipe 31b, the first sealing member 324b is located above the exhaust port 3111b to seal the exhaust port 3111b, so that the exhaust port 3111b is isolated from the exhaust cavity 3113b. When the sleeve pipe 321b moves downward relative to the outer pipe 31b to a fourth position, the first sealing member 324b moves downward to below the exhaust port 3111b, so that the exhaust port 3111b fluidly communicates with the exhaust cavity 3113b.

The second sealing member 325b is disposed on an outer wall of the main body 3226b to seal the opening 3112b and isolate the exhaust cavity 3113b from the opening 3112b. The second sealing member 325b may have an O shape, and is sleeved outside the fourth pipe body 3226b. A second clamping slot 3251b for disposing the second sealing member 325b is provided on an outer side of the fourth pipe body 3226b. The second clamping slot 3251b may be defined on the sixth positioning flange 3224b, or alternatively be independently provided. When the liquid injection pipe 322b is in a first position relative to the sleeve pipe 321b, the second sealing member 325b is in a sealing fit with the second annular retaining ring 3114b to seal the opening 3112b, so that the opening 3112b is isolated from the exhaust cavity 3113b. When the liquid injection pipe 322b moves downward relative to the sleeve pipe 321b to a second position, the second sealing member 325b moves downward to stagger with the second annular retaining ring 3114b, so that the opening 3112b fluidly communicates with the exhaust cavity 3113b. A side surface of the second annular retaining ring 3114b towards the second sealing member 325b may be an inclined surface, to improve the sealing effect.

The third sealing member 326b is disposed on the outer wall of the main body 3226b to isolate the liquid injection port 3221b from the liquid inlet 3121b. The third sealing member 326b may have an O shape, and is sleeved outside the main body 3226b. A third clamping slot 3261b for disposing the third sealing member 326b is provided on an outer side of the main body 3226b. The third clamping slot 3261 may be defined on the positioning member 3227b, or alternatively be independently provided.

The sleeve pipe 321b in some embodiments may include a third pipe section 3216b and a fourth pipe section 3217b disposed at an inner end of the third pipe section 3216b. An inner diameter of the fourth pipe section 3217b is larger than an inner diameter of the third pipe section 3216b, such that a fourth annular retaining ring 3211b is formed at a junction between an inner hole of the third pipe section 3216b and an inner hole of the fourth pipe section 3217b. The fourth annular retaining ring 3211b may be disposed corresponding to the first clamping slot 3241b in an axial position, or alternatively be staggered with the first clamping slot 3241b in the axial position. The third sealing member 326b is in a sealing fit with the fourth annular retaining ring 3211b. When the liquid injection pipe 322b is in the first position relative to the sleeve pipe 321b, the third sealing member 326b is in a sealing fit with the fourth annular retaining ring 3211b to isolate the liquid injection port 3221b from the liquid inlet 3121b. When the liquid injection pipe 322b moves downward relative to the sleeve pipe 321b to the second position, the third sealing member 326b moves downward to stagger with the fourth annular retaining ring 3211b, so that the liquid injection port 3221b fluidly communicates with the liquid inlet 3121b. An outer diameter of the third pipe section 3216b may be less than an outer diameter of the fourth pipe section 3217b, so that a sufficient space is defined between the third pipe section 3216b and a side wall of the first pipe body 311b to discharge the air.

The fourth sealing member 327b is disposed on the outer wall of the main body 3226b. The fourth sealing member 327b may have an O shape, and is sleeved outside the main body 3226b. A fourth clamping slot 3271b for disposing the fourth sealing member 327b is provided on the outer side of the main body 3226b. The fourth sealing member 327b is able to avoid the backflow of the liquid medium in the liquid inlet cavity 3222b, and to minimize the liquid medium remaining in the pipe after injection. Two side surfaces of the fourth annular retaining ring 3211b towards the third sealing member 326b and the fourth sealing member 327b respectively may be inclined surfaces, which facilitate manufacture and improve the sealing effect.

In some embodiments, a ninth positioning flange 3116b may be provided radially inside the first pipe body 311b, and a tenth positioning flange 3229b may be provided radially at an outer periphery of an inner end of the sleeve pipe 321b. An outer end surface of the tenth positioning flange 3229b movably abuts against the ninth positioning flange 3116b, so that the sleeve pipe 321b is elastically maintained in the third position by the elastic member 323b.

In some embodiments, a friction force between the liquid injection pipe 322b and the sleeve pipe 321b is less than a friction force between the sleeve pipe 321b and the outer pipe 31b. An inner hole of an outer end of the liquid injection pipe 322b may be flared to facilitate connection and injection. As shown in FIG. 17, when no liquid injection is needed, the liquid injection pipe 322b is in the first position relative to the sleeve pipe 321b, and the sleeve pipe 321b is in the third position relative to the outer pipe 31b; at this time, the liquid injection passage and the exhaust passage are closed, and two ends of the liquid injection pipe 322b and of the sleeve pipe 321b are retracted into the outer pipe 31b. When a liquid injection needs to be performed, the liquid injection pipe 322b is pressed down, the liquid injection pipe 322b moves downward from the first position to the second position relative to the sleeve pipe 321b, and the sixth positioning flange 3224b on the liquid injection pipe 322b abuts against the outer end surface of the sleeve pipe 321b, the third sealing member 326b moves downward to stagger with the fourth annular retaining ring 3211b on the sleeve pipe 321b, so that the liquid injection port 3221b fluidly communicates with the liquid inlet 3121b to open the liquid injection passage is opened, and the second sealing member 325b moves downward to stagger with the opening 3112b, so that the exhaust cavity 3113b fluidly communicates with the opening 3112b. Continuing to press the liquid injection pipe 322b, the liquid injection pipe 322b will drive the sleeve pipe 321b to move downward together and enable the sleeve pipe 321b to move downward relative to the outer pipe 31b from the third position to the fourth position; at this time, an inner end surface of the sleeve pipe 321b abuts against an outer end surface of the base body 312, the first sealing member 324b moves downward to below the exhaust port 3111b, so that the exhaust port 3111b fluidly communicates with the exhaust cavity 3113b, and the exhaust passage is opened, as shown in FIG. 18. After the liquid injection is finished, a pressing force on the liquid injection pipe 322b is removed, the liquid injection pipe 322b returns from the second position to the first position under the action of the elastic member 323b, such that the liquid injection passage is closed, and the opening 3112b is sealed. Then, the liquid injection pipe 322b continues to drive the sleeve pipe 321b to move and enables the sleeve pipe 321b to return from the fourth position to the third position, so that the exhaust passage is closed.

Figure 19:
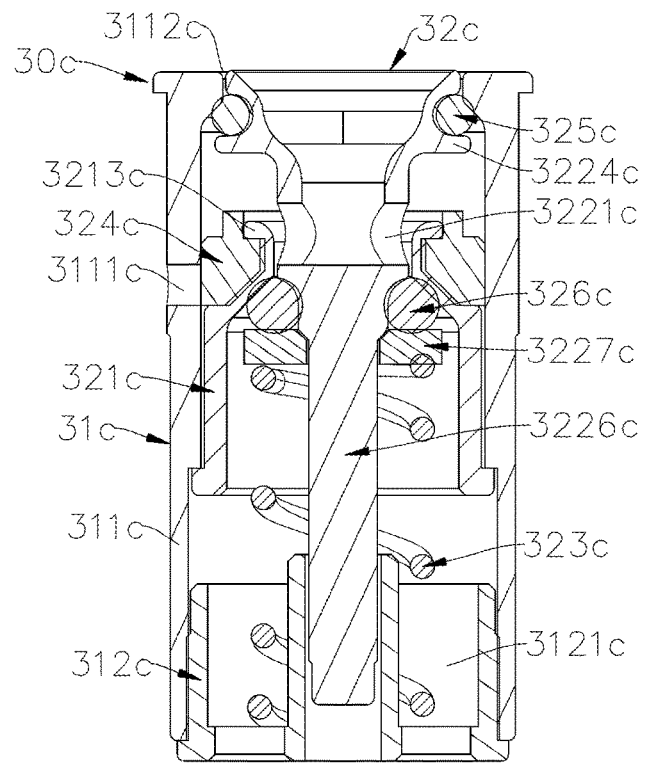
FIG. 19 is a sectional view of a liquid injection structure according to a fourth embodiment of the present disclosure when a liquid injection pipe is in a first position and a sleeve pipe is in a third position.
Figure 20:
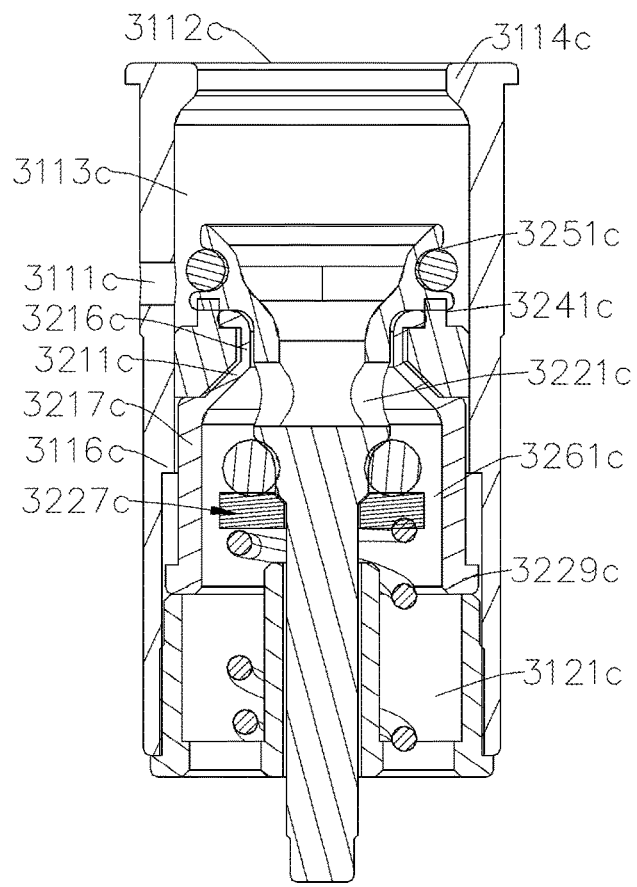
FIG. 20 is a sectional view of the liquid injection structure shown in FIG. 19 when the liquid injection pipe is in a second position and the sleeve pipe is in a fourth position.

FIGS. 19 and 20 show a liquid injection structure 30c in a fourth embodiment of the present disclosure. Compared with the third embodiment, a liquid injection assembly 32c in this embodiment only includes a first sealing member 324c and a second sealing member 325c for respectively sealing the bottom and the top of the exhaust passage, and a third sealing member 326c for sealing the bottom of a liquid injection port 3221c.

Similar to the third embodiment, a liquid injection pipe 322c in this embodiment may include a main body 3226c and a positioning member 3227c detachably sleeved outside the main body 3226c. The main body 3226c extends in a sleeve pipe 321c, and two ends of the main body 3226c extend out of a sleeve pipe 321c. A sixth positioning flange 3224c may be provided outside the main body 3226c, and the sixth positioning flange 3224c movably abuts against an outer end surface of the sleeve pipe 321c. The positioning member 3227c in some embodiments may be a gasket, for mounting an elastic member 323c and a third sealing member 326c.

An outer pipe 31c includes a first pipe body 311c and a base body 312c axially plugged at an inner end of the first pipe body 311c, and the base body 312c may be axially provided with a liquid inlet 3121c fluidly communicating with the liquid storage cavity 11. An inner periphery of an outer end of the first pipe body 311c is radially provided with a second annular retaining ring 3114c, and an inner hole of the second annular retaining ring 3114c defines an opening 3112c. The elastic member 323c is sleeved outside the liquid injection pipe 322c, and two ends of the elastic member 323c abut against the positioning member 3227c and the base body 312c, respectively.

An exhaust port 3111c is defined on a side wall of the first pipe body 311c. An exhaust cavity 3113c is defined between an inner wall of the first pipe body 311c and an outer wall of a liquid injection assembly 32c. The exhaust port 3111c, the exhaust cavity 3113c and the opening 3112c fluidly communicate in sequence to form an exhaust passage that fluidly connects the liquid storage cavity 11 with the outside. A liquid inlet cavity 3222c is defined between an outer wall of the liquid injection pipe 322c and inner walls of the sleeve pipe 321c and the base body 312c. The liquid injection port 3221c, the liquid inlet cavity 3222c and the liquid inlet 3121c fluidly communicate in sequence to form a liquid inlet passage that fluidly connects the liquid inlet 3221c with the liquid storage cavity 11.

The first sealing member 324c is disposed on an outer wall of the sleeve pipe 321c to isolate the exhaust port 3111c from the exhaust cavity 3113c. The first sealing member 324c may have an annular shape, and is sleeved outside the sleeve pipe 321c. A first clamping slot 3241c for disposing the first sealing member 324c is provided on an outer side of the sleeve pipe 321c. An outer periphery of an outer end of the sleeve pipe 321c may be radially provided with a fifth annular retaining ring 3213c, and the first clamping slot 3241c may be defined on the fifth annular retaining ring 3213c. When the sleeve pipe 321c is in a third position relative to the outer pipe 31c, the first sealing member 324c is correspondingly located at the exhaust port 3111c to seal the exhaust port 3111c, so that the exhaust port 3111c is isolated from the exhaust cavity 3113c. When the sleeve pipe 321c moves downward relative to the outer pipe 31c to a fourth position, the first sealing member 324c moves downward to stagger with the exhaust port 3111c, so that the exhaust port 3111c fluidly communicates with the exhaust cavity 3113c.

The second sealing member 325c is disposed on an outer wall of the main body 3226c to seal the opening 3112c and isolate the exhaust cavity 3113c from the opening 3112c. The second sealing member 325c may have an O shape, and is sleeved outside a fourth pipe body 3226c. A second clamping slot 3251c for disposing the second sealing member 325c is provided on an outer side of the fourth pipe body 3226c. The second clamping slot 3251c may be defined on the sixth positioning flange 3224c, or alternatively be independently provided. When the liquid injection pipe 322c is in a first position relative to the sleeve pipe 321c, the second sealing member 325c is in a sealing fit with the second annular retaining ring 3114c to seal the opening 3112c, so that the opening 3112c is isolated from the exhaust cavity 3113c. When the liquid injection pipe 322c moves downward relative to the sleeve pipe 321c to a second position, the second sealing member 325c moves downward to stagger with the second annular retaining ring 3114c, so that the opening 3112c fluidly communicates with the exhaust cavity 3113c. A side surface of the second annular retaining ring 3114c towards the second sealing member 325c may be an inclined surface, which facilitates manufacture and improves the sealing effect.

The third sealing member 326c is disposed on an outer wall of the main body 3226c to isolate the liquid injection port 3221c from the liquid inlet 3121c. The third sealing member 326c may have an O shape, and is sleeved outside the main body 3226c. A third clamping slot 3261c for disposing the third sealing member 326c is provided on an outer side of the main body 3226c. The third clamping slot 3261c may be defined on the positioning member 3227c, or alternatively be independently provided.

The sleeve pipe 321c in some embodiments may include a third pipe section 3216c and a fourth pipe section 3217c disposed at an inner end of the third pipe section 3216c. An inner diameter and an outer diameter of the fourth pipe section 3217c are respectively larger than those of the third pipe section 3216c. A fourth annular retaining ring 3211c is formed at a junction between the third pipe section 3216c and the fourth pipe section 3217c. The fourth annular retaining ring 3211c may be disposed corresponding to the first clamping slot 3241c in an axial position, or alternatively be staggered with the first clamping slot 3241c in the axial position. The third sealing member 326c is in a sealing fit with the fourth annular retaining ring 3211c. When the liquid injection pipe 322c is in the first position relative to the sleeve pipe 321c, the third sealing member 326c is in a sealing fit with the fourth annular retaining ring 3211c to isolate the liquid injection port 3221c from the liquid inlet 3121c. When the liquid injection pipe 322c moves downward relative to the sleeve pipe 321c to the second position, the third sealing member 326c moves downward to stagger with the fourth annular retaining ring 3211c, so that the liquid injection port 3221c fluidly communicates with the liquid inlet 3121c. A side surface of the fourth annular retaining ring 3211c towards the third sealing member 326c may be an inclined surface, which facilitates manufacture and improves the sealing effect.

In some embodiments, a ninth positioning flange 3116c may be provided radially inside the first pipe body 311c, and a tenth positioning flange 3229c may be provided radially at an outer periphery of an inner end of the sleeve pipe 321c. An outer end surface of the tenth positioning flange 3229c movably abuts against an outer end surface of the ninth positioning flange 3116c, so that the sleeve pipe 321c is able to be elastically maintained in the third position by the elastic member 323c.

In some embodiments, a friction force between the liquid injection pipe 322c and the sleeve pipe 321c is less than a friction force between the sleeve pipe 321c and the outer pipe 31c. An inner hole at an outer end of the liquid injection pipe 322c may be flared to facilitate connection and injection. As shown in FIG. 19, when no liquid injection is needed, the liquid injection pipe 322c is in the first position relative to the sleeve pipe 321c, and the sleeve pipe 321c is in the third position relative to the outer pipe 31c; at this time, both the liquid injection passage and the exhaust passage are closed, and two ends of the liquid injection pipe 322c and the sleeve pipe 321c are retracted into the outer pipe 31c. When a liquid injection needs to be performed, the liquid injection pipe 322c is pressed down, the liquid injection pipe 322c moves downward from the first position to the second position relative to the sleeve pipe 321c, and the sixth positioning flange 3224c on the liquid injection pipe 322c abuts against the outer end surface of the sleeve pipe 321c, the third sealing member 326c moves downward to stagger with the fourth annular retaining ring 3211c on the sleeve pipe 321c, so that the liquid injection port 3221c fluidly communicates with the liquid inlet 3121c, and the liquid injection passage is opened; and the second sealing member 325c moves downward to stagger with the opening 3112c, so that the exhaust cavity 3113c fluidly communicates with the opening 3112c. Continuing to press the liquid injection pipe 322c, the liquid injection pipe 322c drives the sleeve pipe 321c to move downward together and enables the sleeve pipe 321c to move downward relative to the outer pipe 31c from the third position to the fourth position; at this time, an inner end surface of the sleeve pipe 321c abuts against an outer end surface of the base body 312, the first sealing member 324c moves downward to below the exhaust port 3111c, so that the exhaust port 3111e fluidly communicates with the exhaust cavity 3113c, and the exhaust passage is opened, as shown in FIG. 20. After the liquid injection is finished, a pressing force on the liquid injection pipe 322c is removed, the liquid injection pipe 322c returns from the second position to the first position under the action of the elastic member 323c, the liquid injection passage is closed, and the opening 3112c is sealed. Then, the liquid injection pipe 322c continues to drive the sleeve pipe 321c to move and enables the sleeve pipe 321c to return from the fourth position to the third position, so that the exhaust passage is closed.

Compared with the prior art, the liquid injection port of the liquid injection structure of the present disclosure is much closer to an outer surface of the product, that is, the position of the liquid injection port on the liquid injection pipe is much closer to the position of the flared opening of the liquid injection pipe. Therefore, the liquid medium remaining in the pipe after injection can be reduced as much as possible, and the cleaning is much easier.

It should be understood that the above technical features can be arbitrarily combined without limitation.

Although the preferred implementations of the present disclosure are described in detail above, they should not be construed as a limitation to the patent scope of the present disclosure. It should be noted that for those of ordinary skill in the art the above technical features can be freely combined and several modifications and improvements can be made without departing from the concept of the present disclosure. However, all equivalent transformations and modifications made within the scope of the claims of the present disclosure should fall within the scope of the claims of the present disclosure.

What is claimed is:

1. A liquid injection structure for an atomizer, wherein the liquid injection structure comprises an outer pipe and a liquid injection assembly disposed in the outer pipe; the outer pipe is provided with an exhaust port;
   the liquid injection assembly comprises a sleeve pipe and a liquid injection pipe, and the liquid injection pipe is provided with a liquid injection port;
   the liquid injection pipe is axially disposed in the sleeve pipe, and is axially movable back and forth relative to the sleeve pipe between a first position adjacent to an outer end of the outer pipe and a second position away from the outer end of the outer pipe; when the liquid injection pipe is in the first position, the sleeve pipe seals the liquid injection port; when the liquid injection pipe is in the second position, the seal of the liquid injection port by the sleeve pipe is released; and the sleeve pipe is axially disposed in the outer pipe, and is axially movable back and forth relative to the outer pipe between a third position adjacent to the outer end of the outer pipe and a fourth position away from the outer end of the outer pipe; when the sleeve pipe is in the third position, the sleeve pipe seals the exhaust port; when the sleeve pipe is in the fourth position, the seal of the exhaust port by the sleeve pipe is released.

2. The liquid injection structure according to claim 1, wherein the outer pipe comprises a first pipe body; the exhaust port is defined on a side wall of the first pipe body; an outer end of the first pipe body is provided with an opening; an exhaust cavity is defined between an inner wall of the first pipe body and an outer wall of the liquid injection assembly; the exhaust port, the exhaust cavity and the opening are fluidly connected in sequence to form an exhaust passage.

3. The liquid injection structure according to claim 2, wherein the outer pipe further comprises a base body disposed at an inner end of the first pipe body, and the base body is provided with a liquid inlet; a liquid inlet cavity is defined between an outer wall of the liquid injection pipe and inner walls of the sleeve pipe and the base body; the liquid injection port, the liquid inlet cavity and the liquid inlet are fluidly connected in sequence to form a liquid inlet passage.

4. The liquid injection structure according to claim 3, wherein the liquid injection assembly further comprises an elastic member; two ends of the elastic member respectively abut against the liquid injection pipe and the base body to elastically maintain the liquid injection pipe in the first position and elastically maintain the sleeve pipe in the third position.

5. The liquid injection structure according to claim 4, wherein when the liquid injection pipe is pressed, the liquid injection pipe moves from the first position to the second position to abut against the sleeve pipe, and the liquid injection port fluidly communicates with the liquid inlet to open the liquid inlet passage; continuing to press the liquid injection pipe, the liquid injection pipe drives the sleeve pipe to move together to enable the sleeve pipe to move from the third position to the fourth position to abut against the base body, and the exhaust port fluidly communicates with the opening to open the exhaust passage;

when a pressing force on the liquid injection pipe is removed, the liquid injection pipe returns from the second position to the first position under an action of the elastic member, so that the liquid injection port is isolated from the liquid inlet to close the liquid inlet passage; then, the liquid injection pipe drives the sleeve pipe to return from the fourth position to the third position, so that the exhaust port is isolated from the opening to close the exhaust passage.

6. The liquid injection structure according to claim 1, wherein a friction force between the liquid injection pipe and the sleeve pipe is less than a friction force between the sleeve pipe and the outer pipe.

7. The liquid injection structure according to claim 4, wherein the liquid injection structure further comprises a first sealing member and a third sealing member; and the first sealing member is disposed on a side wall of the sleeve pipe to isolate the exhaust port from the exhaust cavity, and the third sealing member is disposed on a side wall of the liquid injection pipe to isolate the liquid injection port from the liquid inlet.

8. The liquid injection structure according to claim 7, wherein the liquid injection structure further comprises a second sealing member, and the second sealing member is fitted at the opening to seal the opening and isolate the exhaust cavity from the opening.

9. The liquid injection structure according to claim 8, further comprising a fourth sealing member provided on a side wall of the liquid injection pipe, wherein the third sealing member and the fourth sealing member are respectively located on two opposite sides of the liquid injection port.

10. The liquid injection structure according to claim 8, wherein an inner periphery of the outer end of the first pipe body is radially provided with a second annular retaining ring, and an inner hole of the second annular retaining ring defines the opening;

the second sealing member is disposed on a side of the second annular retaining ring towards the base body, and the second sealing member is in a sealing fit with the second annular retaining ring.

11. The liquid injection structure according to claim 10, wherein an inner periphery of an outer end of the sleeve pipe is radially provided with a third annular retaining ring; when the liquid injection pipe is in the first position, an outer end surface of the liquid injection pipe abuts against the third annular retaining ring; and when the liquid injection pipe is in the second position, the outer end surface of the liquid injection pipe is spaced from the third annular retaining ring.

12. The liquid injection structure according to claim 11, wherein the sleeve pipe comprises a third pipe body axially disposed in the first pipe body and a second pipe body axially inserted at an outer end of the third pipe body; an inner periphery of an outer end of the second pipe body radially extends inwards to form the third annular retaining ring;

a first annular retaining ring is provided outside the second pipe; an inner end surface of the first annular retaining ring abuts against the third pipe body, and an outer end surface of the first annular retaining ring abuts against the second sealing member;

the first sealing member is sleeved outside the third pipe body, and the third sealing member is in a sealing fit with an inner end surface of the second pipe body.

13. The liquid injection structure according to claim 10, wherein two ends of the liquid injection pipe extend out of the sleeve pipe respectively, and the second sealing member is disposed on a side wall of the liquid injection pipe.

14. The liquid injection structure according to claim 13, wherein the sleeve pipe comprises a third pipe section and a fourth pipe section provided at an inner end of the third pipe section; an inner diameter of the third pipe section is less than an inner diameter of the fourth pipe section; a fourth annular retaining ring is formed at a junction between an inner hole of the third pipe section and an inner hole of the fourth pipe section; the third sealing member is in a sealing fit with the fourth annular retaining ring.

15. The liquid injection structure according to claim 14, wherein the liquid injection pipe comprises a fourth pipe body and a fifth pipe body sleeved outside an inner end of the fourth pipe body; the liquid injection port is defined on the fourth pipe body; the second sealing member is sleeved outside the fourth pipe body, and the third sealing member is sleeved outside the fifth pipe body.

16. The liquid injection structure according to claim 15, wherein a sixth positioning flange is provided outside the fourth pipe body; an outer end surface of the sixth positioning flange abuts against the second sealing member, and an inner end surface of the sixth positioning flange movably abuts against an outer end surface of the sleeve pipe;

an eighth positioning flange is provided outside the fifth pipe body; an outer end surface of the eighth positioning flange abuts against the third sealing member, and an inner end surface of the eighth positioning flange abuts against the elastic member.

17. The liquid injection structure according to claim 14, wherein the liquid injection pipe comprises a main body and a positioning member detachably sleeved outside the main body; an outer end surface of the positioning member abuts against the third sealing member, and an inner end surface of the positioning member abuts against the elastic member.

18. An atomizer, comprising a liquid storage cavity and a liquid injection structure, wherein the liquid injection structure is disposed on a cavity wall forming the liquid storage cavity; a liquid inlet and an exhaust port of the liquid injection structure are respectively in fluid communication with the liquid storage cavity;

the liquid injection structure comprises an outer pipe and a liquid injection assembly disposed in the outer pipe; the outer pipe is provided with the exhaust port;

the liquid injection assembly comprises a sleeve pipe and a liquid injection pipe, and the liquid injection pipe is provided with a liquid injection port;

the liquid injection pipe is axially disposed in the sleeve pipe, and is axially movable back and forth relative to the sleeve pipe between a first position adjacent to an outer end of the outer pipe and a second position away from the outer end of the outer pipe; when the liquid injection pipe is in the first position, the sleeve pipe seals the liquid injection port; when the liquid injection pipe is in the second position, the seal of the liquid injection port by the sleeve pipe is released; and the sleeve pipe is axially disposed in the outer pipe, and is axially movable back and forth relative to the outer pipe between a third position adjacent to the outer end of the outer pipe and a fourth position away from the outer end of the outer pipe; when the sleeve pipe is in the third position, the sleeve pipe seals the exhaust port; when the sleeve pipe is in the fourth position, the seal of the exhaust port by the sleeve pipe is released.

19. The atomizer according to claim 18, further comprising an atomization unit and a suction nozzle slidably disposed at one end of the atomization unit, wherein the liquid storage cavity is defined in the atomization unit; the suction nozzle is able to move back and forth relative to the atomization unit between a fifth position and a sixth position;

the liquid injection structure is disposed at an end of the atomization unit towards the suction nozzle; when the suction nozzle is in the fifth position, the liquid injection structure is covered by the suction nozzle; and when the suction nozzle is in the sixth position, the liquid injection structure is exposed.

20. An electronic atomizing device, comprising a power supply device and an atomizer electrically connected to the power supply device, wherein the atomizer comprises a liquid storage cavity and a liquid injection structure disposed on a cavity wall forming the liquid storage cavity; a liquid inlet and an exhaust port of the liquid injection structure are respectively in fluid communication with the liquid storage cavity;

the liquid injection structure comprises an outer pipe and a liquid injection assembly disposed in the outer pipe; the outer pipe is provided with the exhaust port;

the liquid injection assembly comprises a sleeve pipe and a liquid injection pipe, and the liquid injection pipe is provided with a liquid injection port;

the liquid injection pipe is axially disposed in the sleeve pipe, and is axially movable back and forth relative to the sleeve pipe between a first position adjacent to an outer end of the outer pipe and a second position away from the outer end of the outer pipe; when the liquid injection pipe is in the first position, the sleeve pipe seals the liquid injection port; when the liquid injection pipe is in the second position, the seal of the liquid injection port by the sleeve pipe is released; and the sleeve pipe is axially disposed in the outer pipe, and is axially movable back and forth relative to the outer pipe between a third position adjacent to the outer end of the outer pipe and a fourth position away from the outer end of the outer pipe; when the sleeve pipe is in the third position, the sleeve pipe seals the exhaust port; when the sleeve pipe is in the fourth position, the seal of the exhaust port by the sleeve pipe is released.

* * * * *